US010398381B1

(12) United States Patent
Heneghan et al.

(10) Patent No.: US 10,398,381 B1
(45) Date of Patent: Sep. 3, 2019

(54) SYSTEM AND METHOD FOR CHARACTERIZING CARDIAC ARRHYTHMIA

(71) Applicant: FITBIT, INC., San Francisco, CA (US)

(72) Inventors: Conor Heneghan, Campbell, CA (US); Alexandros Pantelopoulos, San Francisco, CA (US); Subramaniam Venkatraman, Walnut Creek, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 15/356,383

(22) Filed: Nov. 18, 2016

Related U.S. Application Data

(60) Provisional application No. 62/257,600, filed on Nov. 19, 2015.

(51) Int. Cl.
*A61B 5/00* (2006.01)
*A61B 5/026* (2006.01)
*A61B 5/0464* (2006.01)

(52) U.S. Cl.
CPC .............. *A61B 5/721* (2013.01); *A61B 5/002* (2013.01); *A61B 5/0022* (2013.01); *A61B 5/0261* (2013.01); *A61B 5/4818* (2013.01); *A61B 5/6814* (2013.01); *A61B 5/6815* (2013.01); *A61B 5/6824* (2013.01); *A61B 5/742* (2013.01); *A61B 5/746* (2013.01); *A61B 5/0464* (2013.01)

(58) Field of Classification Search
CPC ....... A61B 5/0402; A61B 5/08; A61B 5/1135; A61B 5/14551
See application file for complete search history.

(56) References Cited

U.S. PATENT DOCUMENTS

| | | | |
|---|---|---|---|
| 6,361,501 B1 * | 3/2002 | Amano | A61B 5/02028 600/485 |
| 7,794,406 B2 * | 9/2010 | Reisfeld | A61B 5/0402 600/479 |
| 8,974,396 B1 | 3/2015 | Brady et al. | |
| 9,144,385 B1 | 9/2015 | Brady et al. | |
| 9,179,849 B1 | 11/2015 | Brady et al. | |
| 9,314,174 B1 | 4/2016 | Brady et al. | |
| 2004/0215095 A1 * | 10/2004 | Lee | A61B 5/14551 600/529 |
| 2011/0270049 A1 * | 11/2011 | Katra | A61B 5/0002 600/301 |
| 2012/0310100 A1 * | 12/2012 | Galen | A61B 5/726 600/500 |

\* cited by examiner

*Primary Examiner* — Joseph M Santos Rodriguez
(74) *Attorney, Agent, or Firm* — Weaver Austin Villeneuve & Sampson LLP

(57) ABSTRACT

In an embodiment, a data processing method comprises obtaining one or more photoplethysmography (PPG) signals from one or more PPG sensors of a monitoring apparatus, the PPG signals being generated based upon optically detecting pulsed variations in blood flow; obtaining a motion sensor signal from a motion sensor in the monitoring apparatus; identifying, based upon the motion sensor signal, one or more periods of motion (e.g., low motion) of the monitoring apparatus; and selectively obtaining and storing segments of the PPG signals based on a temporal relationship between the segments of the PPG signals and the identified periods of motion.

30 Claims, 14 Drawing Sheets

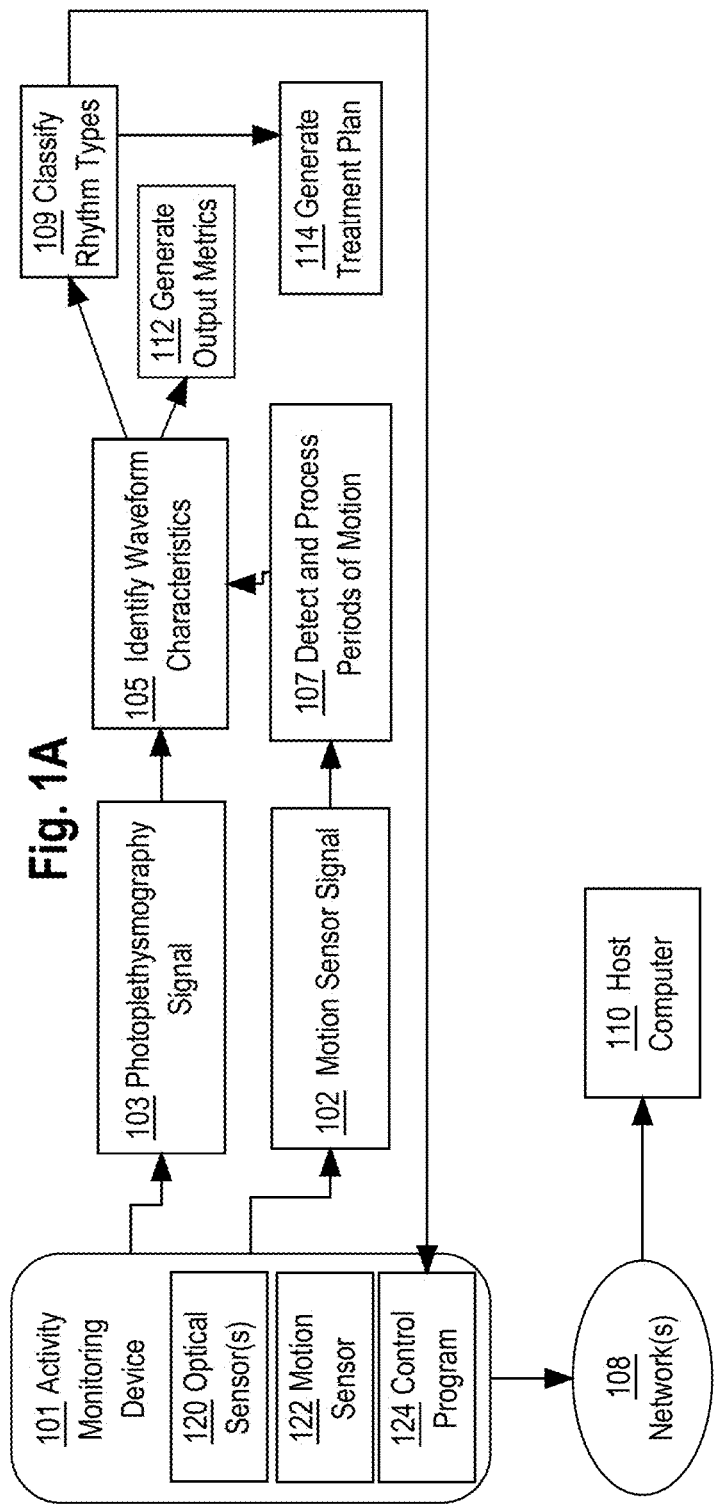

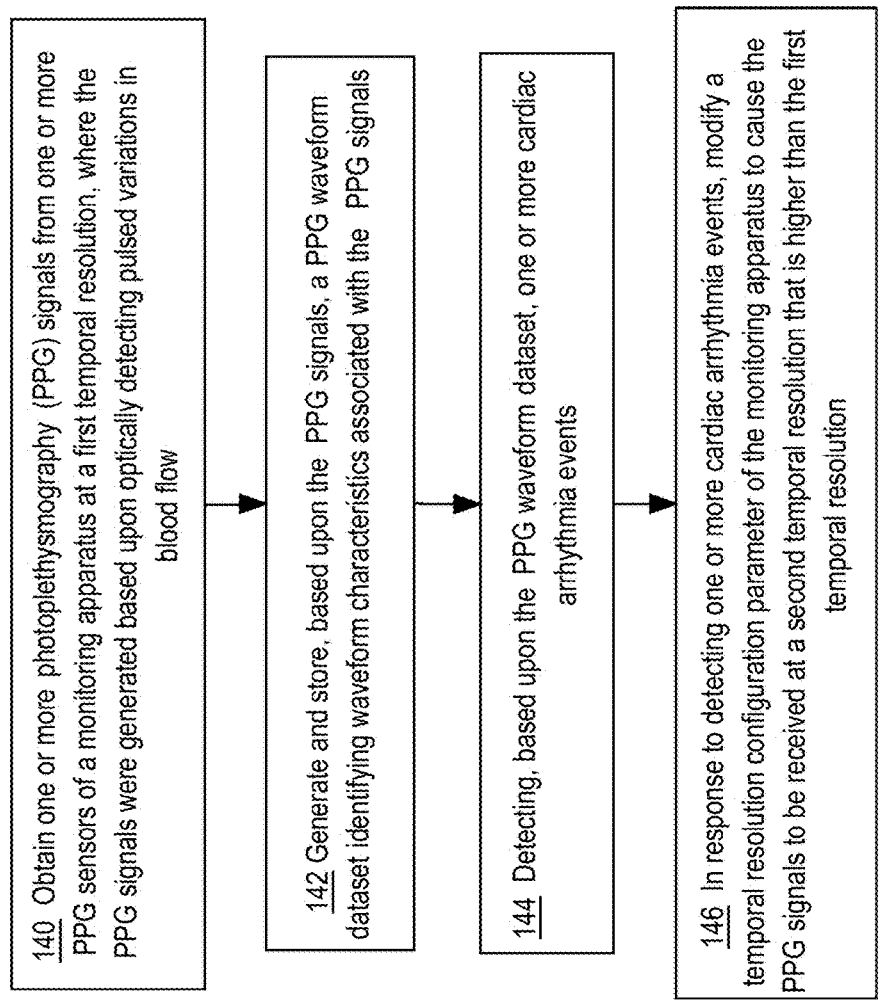

Fig. 1C

140 Obtain one or more photoplethysmography (PPG) signals from one or more PPG sensors of a monitoring apparatus at a first temporal resolution, where the PPG signals were generated based upon optically detecting pulsed variations in blood flow 142 Generate and store, based upon the PPG signals, a PPG waveform dataset identifying waveform characteristics associated with the PPG signals 144 Detecting, based upon the PPG waveform dataset, one or more cardiac arrhythmia events 146 In response to detecting one or more cardiac arrhythmia events, modify a temporal resolution configuration parameter of the monitoring apparatus to cause the PPG signals to be received at a second temporal resolution that is higher than the first temporal resolution

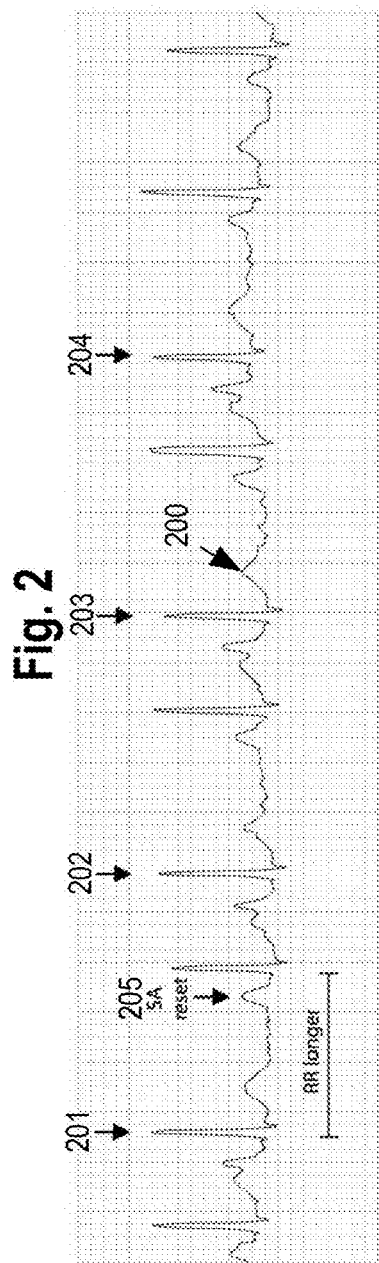

SYSTEM AND METHOD FOR CHARACTERIZING CARDIAC ARRHYTHMIA

CROSS-REFERENCE TO RELATED APPLICATIONS; BENEFIT CLAIM

This application claims the benefit of Provisional Application No. 62/257,600, filed Nov. 19, 2015, the entire contents of which are hereby incorporated by reference as if fully set forth herein, under 35 U.S.C. § 119(e).

FIELD OF THE DISCLOSURE

The present disclosure generally relates to computer-implemented techniques for characterizing cardiac arrhythmias. The disclosure relates more specifically to programmed activity monitoring devices, computer programs, algorithms and methods that can be used to characterize cardiac arrhythmias.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

In humans, an arrhythmia is an anomaly in heart function in which heartbeats do not conform to normal sinus rhythm and thus beat abnormally. Typically, detecting arrhythmia requires using sensor apparatus that is uncomfortable or inconvenient for the patient to use or wear. For example, measurement of heart function by electrocardiogram (ECG or EKG) requires applying electrical leads to the patient's torso, typically with a sticky adhesive and a conductive gel. In some cases a portable apparatus such as the Holter monitor may be used. These approaches create inconvenience to the patient as their movement may be restricted, or they may be unable to shower or bathe during the period of wearing the electrodes.

BRIEF DESCRIPTION OF THE DRAWINGS

In the drawings:

FIG. 1A illustrates general data flow and data processing according to an embodiment.

FIG. 1C illustrates an example process of dynamically changing the temporal frequency at which PPG data is obtained in response to detecting an arrhythmia event.

FIG. 2 is a graph of an example cardiac arrhythmia caused by premature atrial contractions.

DETAILED DESCRIPTION

Figure 1B:
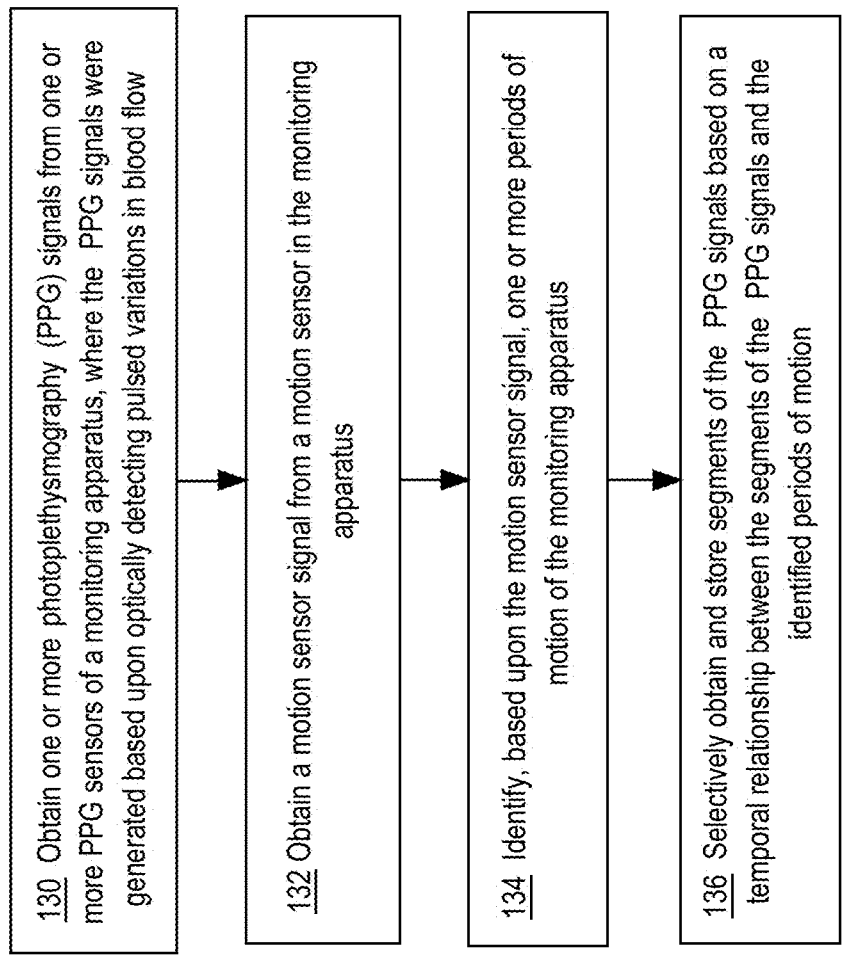
FIG. 1B illustrates an example process of selectively storing segments of PPG signals.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Embodiments are described in sections below according to the following outline:
1. General Overview
2. Example Implementation for Detecting Atrial Fibrillation
   2.1 The Root Mean Square of Successive Differences ("RMSSD") Approach
   2.2 Assessment of Correlated Sympathetic or Parasympathetic Activity
   2.3 PPG Waveform Shape Analysis
   2.4 Integration with Mobile Computing and Cloud-Based Devices
3. Characterization of Other Arrhythmias
4. Benefits of Certain Embodiments
5. Hardware Overview
5.1 Activity Monitoring Device
5.2 Host Computer
6. Extensions and Alternatives 1. General Overview In an embodiment, a data processing method comprises obtaining one or more photoplethysmography (PPG) signals from one or more PPG sensors of a monitoring apparatus, the PPG signals being generated based upon optically detecting pulsed variations in blood flow; obtaining a motion sensor signal from a motion sensor in the monitoring apparatus; identifying, based upon the motion sensor signal, one or more periods of motion of the monitoring apparatus; selectively obtaining and storing segments of the PPG signals based on a temporal relationship between the segments of the PPG signals and the identified periods of motion.

According to one feature, the method may further comprise generating and storing, based upon the PPG signals, PPG waveform data identifying waveform characteristics associated with the PPG signals; and based upon the PPG waveform data and the one or more periods of motion, generating and storing, based on PPG waveform data, arrhythmia event data describing one or more arrhythmia events.

In another aspect, the disclosure provides a data processing method that comprises obtaining, at a server computer, one or more of photoplethysmography (PPG) signals or PPG waveform data identifying waveform characteristics associated with the PPG signals from a monitoring apparatus via a wireless communication link, the PPG signals and the PPG waveform data not including PPG data associated with detected periods of motion of the monitoring apparatus; obtaining, at the server computer, a call to an application programming interface (API) of the server computer that requests one or more of the PPG signals or the PPG waveform data; and in response to the call, transmitting, from the server computer to a host computer that transmitted the call, the requested PPG signals or PPG waveform data.

In a further aspect, an activity monitoring device comprises one or more processors coupled to electronic digital memory; in the memory, one or more sequences of programmed instructions which when executed by the one or more processors cause the one or more processors to perform: obtaining one or more photoplethysmography (PPG) signals from one or more PPG sensors of a monitoring apparatus, the PPG signals being generated based upon optically detecting pulsed variations in blood flow; obtaining a motion sensor signal from a motion sensor in the monitoring apparatus; identifying, based upon the motion sensor signal, one or more periods of motion of the monitoring apparatus; and selectively obtaining and storing segments of the PPG signals based on a temporal relationship between the segments of the PPG signals and the identified periods of motion.

In yet another aspect, a method of treatment of the human body comprises obtaining one or more photoplethysmography (PPG) signals from one or more PPG sensors of a monitoring apparatus, the PPG signals being generated based upon optically detecting pulsed variations in blood flow; obtaining a motion sensor signal from a motion sensor in the monitoring apparatus; identifying, based upon the motion sensor signal, one or more periods of motion of the monitoring apparatus; selectively obtaining and storing segments of the PPG signals based on a temporal relationship between the segments of the PPG signals and the identified periods of motion; generating and storing, based on the segments of the PPG signals, PPG waveform data identifying waveform characteristics associated with the PPG signals; generating and storing, based on PPG waveform data, arrhythmia event data describing one or more arrhythmia events; and based on the arrhythmia event data describing the one or more arrhythmia events, generating and transmitting to a user associated with the monitoring apparatus, an electronic digital recommendation message comprising a recommendation for treatment of the one or more arrhythmia events.

In still another aspect, a data processing method comprises obtaining one or more photoplethysmography (PPG) signals from one or more PPG sensors of a monitoring apparatus at a first temporal resolution, the PPG signals being generated based upon optically detecting pulsed variations in blood flow; generating and storing, based upon the PPG signals, a PPG waveform dataset identifying waveform characteristics associated with the PPG signals; detecting, based upon the PPG waveform dataset, one or more cardiac arrhythmia events; and in response to detecting, based on the PPG waveform dataset, the one or more cardiac arrhythmia events, modifying a temporal resolution configuration parameter of the monitoring apparatus to cause the PPG signals to be received at a second temporal resolution that is higher than the first temporal resolution.

In one embodiment, computer-implemented techniques can identify cardiac arrhythmias in humans based upon processing data representing the rhythm of the heart that has been obtained by monitoring the pulse photoplethysmogram (PPG) of the blood flow arising from the heart.

In one embodiment, one or more PPG sensors in a personal activity monitoring device are used to acquire PPG signals representing heartbeat and/or heart rhythm. In various embodiments, the activity monitoring device may be configured or adapted to be worn on the wrist, fingertip, ear, or forehead. In general embodiments may be configured to be worn or attached to any surface of the body having characteristics of the skin and blood vessels that permit an external, non-invasive apparatus to optically detect PPG signals representative of blood flow.

As further described herein, the particular hardware elements used to implement different embodiments may vary, but in one embodiment, an activity monitoring device comprises at least one motion sensor, one or more optical sensors, a digital processor such as a microcontroller or CPU, and digital memory storing instructions implemented as software or firmware that are programmed to determine intervals of heart rhythm based, for example, upon determining time differences between successive signal peaks represented in the acquired signals or data.

In some embodiments, a signal from the motion sensor is used to detect periods of sleep or low motion, and perform analysis of pulse interval data to detect arrhythmia only during those periods. These embodiments recognize that greater blood-oxygen perfusion may occur when the body is warmer during sleep and/or as a result of vasodilation, and that the body at rest produces a more stable PPG signal. Detecting sleep therefore may result in using a better PPG signal and thus better assessment of arrhythmia conditions.

Still other embodiments may use the motion sensor signal to detect periods of exercise or activity, and in response, to trigger use of detection algorithms. In some embodiments, the detection algorithms may implement PPG data collection at a higher frequency for a time period occurring just after the time period of exercise or activity. In this embodiment, computer-based analysis of the rate of arrhythmias in the period of rest soon after an exercise will provide information similar to that obtained with a clinical stress test. The motion sensor can be used to infer the periods of exercise and stillness for which this metric should be measured.

Chronotropic incompetence can be observed by measuring the rate of increase of heart rate in response to physical activity measured with a motion sensor. In one particular embodiment, the motion sensor signal is used to detect periods of exercise or activity, and to trigger measurement of heartbeat as well as changes that could indicate chronotropic incompetence. In yet another embodiment, the system may be programmed to automatically detect the conditions of a cardiac clinical stress test, which typically involve a period of exercise followed by low motion. During the period of low motion soon after exercise, PPG waveform data may be characterized with respect to any of the arrhythmias that are otherwise disclosed herein.

In an embodiment, techniques are provided to detect and discard erroneous pulses in the PPG data.

In another embodiment, low amplitude PPG signals are detected and amplitude values are used to infer arrhythmia.

Embodiments may be programmed or configured to detect several different forms of arrhythmia. For example, embodiments may be programmed or configured to perform any one or more of the following:

Detecting premature atrial contraction using a running average formula

Detecting bradycardia over a timescale that is consistent with sleep apnea

Detecting tachycardia over a timescale that is consistent with sleep apnea

Detecting atrial fibrillation ("AF") and record the amount and duration of the fibrillation (commonly referred to as the "AF burden")

Detecting a drop in heart rate during sleep

Estimating heart rate variability (HRV)

Embodiments also may be programmed or configured to perform, in response to detecting any of the foregoing, increasing the frequency of collecting PPG data using the monitoring apparatus, and/or increasing the frequency of uploading the collected data to another computer, such as a networked or cloud-based server computer, and/or generating one or more alert signals, messages or notifications as output to the monitoring apparatus, another computer, or another device.

Embodiments may include one or more host computers that are coupled by network connections to the monitoring apparatus. A particular host computer may be programmed or configured as a server to a plurality of monitoring devices having the role of clients of the server. The host computer may implement a variety of data characterizing, analysis and/or reporting processes. For example, in one embodiment, a host computer is programmed or configured to request (as by polling), receive (as by pushing), or otherwise obtain periodic updates from the activity monitoring apparatus. Updates may comprise raw PPG signal data collected by the activity monitoring apparatus and/or heartbeat or heart rhythm data or signals that have been formed by the activity monitoring apparatus.

The host computer may be programmed to perform validation or further analysis of any of the physiological conditions listed above, taking advantage of the greater processing power that is typically available at a host computer or server computer as compared to a miniature activity monitoring apparatus that is worn on the body. The host computer also may be programmed or configured to output a variety of metrics including but not limited to heartbeats, sequences, number of abnormal sequences, and other metrics.

Therefore, embodiments herein provide a non-invasive means of monitoring cardiac arrhythmias (such as frequent premature atrial contractions or paroxysmal atrial fibrillation) which provide convenience to both patients and any clinical personnel involved in the care of such patients.

FIG. 1A illustrates general data flow and data processing according to an embodiment. In one example embodiment, an activity monitoring device 101 is worn on the body (e.g., during a period of sleep or activity). The activity monitoring device 101 may be implemented using apparatus having a variety of form factors. In various embodiments, the device 101 comprises a wrist-mounted device, such as the FitBit Charge HR commercially available from Fitbit, Inc., San Francisco, Calif., or a device worn on another body part such as the fingertip, ear, or head. The apparatus such as activity monitoring device 101 comprises at least one motion sensor 122 which measures movement of the body, one or more optical sensors 120 that are configured to measure pulsatile variations in the blood flow in the body (e.g., a portion of the body adjacent to the device 101 when the device 101 is worn), and a control program 124 that implements functions and processes that are further described herein.

The one or more optical sensors 120 generate, as output, a photoplethysmogram (PPG) signal 103. The PPG signal 103 can be acquired, in various embodiments, using green, red or infrared light sources, or with one or more types of light sources simultaneously. The optical sensors 120 may comprise one or more such light sources positioned proximate to a detector. Examples of light sources include light-emitting diodes (LEDs), filament-based lamps, phosphor light sources, and lasers. Examples of detectors include photodiodes, phototransistors, CCD sensors, thermopile detectors, and CMOS camera sensors.

The light emitted by a light source includes wavelength and frequency properties, which are inversely related to one another. Different wavelengths may be more beneficial for the acquisition of a PPG signal under certain operating conditions of the activity monitoring device 101. Operating conditions may include skin pigmentation level, ambient temperature, and/or surface temperature of the skin. For example, the penetration depth of light is dependent on its wavelength. A longer wavelength can penetrate to deeper tissue than a shorter wavelength. Thus, in some instances, based on pigmentation level of the user, it may be preferable to use a light source with a longer wavelength, in order to acquire an accurate PPG signal. In another example, a shorter wavelength may be preferable for acquiring an accurate PPG signal when the ambient temperature and/or surface temperature of the skin is cooler.

Light sources of various wavelengths can be emitted by a light source, including, but not limited to 560 nm, 640 nm, and/or 960 nm. In one embodiment, the wavelength or frequency of the light emitted by the light source may be modified, adjusted, and/or controlled to improve the acquisition of the PPG signal under given operating conditions.

The PPG signal 103 typically comprises signal variations that are associated with each heart beat as blood volume flows through the arteries in the body. As seen at block 105, in an embodiment, the activity monitoring device 101 or a host computer 110 is programmed or configured to identify waveform characteristics based upon the PPG signal. In various embodiments, block 105 may represent programming to extract information about the cardiac rhythm such as peak-to-peak intervals ("PP intervals" or "RR intervals") represented in the PPG signal 130, to compute an area under a curve represented in graph or waveform of the PPG signal 130, or other techniques. Because either the activity monitoring device 101 or a host computer 110 may be programmed or configured to obtain such data and perform other processing, the activity monitoring device and host computer may be termed "the system" for purposes of this disclosure as each constitutes a useful data processing system for the purposes described herein. In an embodiment, time between successive heart beats is measured in seconds and comprises the time between successive peaks of the PPG signal. Various embodiments may use different techniques to extract the RR intervals. For example, the system may find peaks in the PPG signal 130 using template matching.

In various embodiments, the motion sensor signal 102 comprises any of an accelerometer sensor signal from an accelerometer, an altitude signal from an altimeter, a gyroscopic motion signal from a gyroscope, or a geographical position signal from a global positioning system (GPS) receiver. In various embodiments, one or more motion-related metrics may be generated based upon motion sensor signal 102. In one embodiment, a motion-related metric may be data or a value derived or generated based on a motion sensor signal 102, such as a standard of deviation of the motion sensor signal 102. In another embodiment, a motion-related metric of a motion sensor signal 102 is the motion sensor signal 102 itself. In some embodiments, a motion sensor signal 102 may refer to the motion sensor signal data received from motion sensor 122, and in other embodiments, a motion sensor signal 102 may refer to a motion-related metric generated based on motion sensor signal data received from motion sensor 122. In one embodiment, motion sensor 122 comprises a tri-axial accelerometer.

Embodiments recognize that the presence of motion by the body can cause obtaining a poor quality PPG signal 103. In an embodiment, to minimize the possibility of misdetection of PP intervals, a motion sensor signal 102 obtained from motion sensor 122 is used to detect and process periods of motion, as shown at block 107. In various embodiments, processing at block 107 may include steps to mask out or exclude periods of high movement, or to identify periods of sleep for purposes of analysis of conditions such as arrhythmias or sleep apnea during the periods of sleep. The motion sensor signal 102 represents periods of activity of the body as measured by the motion sensor 122. The motion sensor 122 also may be used to infer periods of sleep and to cause the activity monitoring device 101 or host computer 110 to search the data for datasets indicating arrhythmias only during periods of sleep or during particular stages of sleep.

In some embodiments, the activity monitoring device 101 may include a global positioning system (GPS) receiver and a GPS signal from the receiver may be used additionally or as an alternative to the use of the motion sensor signal 102 for detecting motion of the activity monitoring device. Thus, in all instances in this disclosure in which use of the motion sensor 122 or the motion sensor signal 102 are described, a GPS signal could be used as a supplement or a substitute.

Further, embodiments may be programmed or configured to adaptively remove artifacts from the PPG data in response to motion sensor input and/or an expected error rate in the data arising from rotation or movement of the activity monitoring device 101. As one example, adaptive detection of artifacts may comprise continuously comparing windows of PPG data to a template, and in response to detecting aberrations, removing artifacts in the PPG data to more closely match the template. By using the motion sensor signal 102 as a trigger, this approach prevents removing artifacts too aggressively by presuming that the PPG data is correct (and thus will not be removed) unless both the motion sensor signal 102 indicates motion and a poor match to a template is found. Additionally or alternatively, the control program 124 may implement filtering processes to filter out low-frequency noise in the PPG data, where such noise may be caused by breathing.

Based upon the PP intervals that have been determined at block 105, and excluding periods of motion as seen at block 107, in an embodiment, the resulting data may be used to classify the PPG data as indicating one or more heart rhythm types, as seen at block 109.

FIG. 1B illustrates an example process of selectively storing segments of PPG signals. In one embodiment, FIG. 1B may serve as an algorithm that may be used as a basis for programming instructions for control program 124. Block 130 comprises obtaining one or more photoplethysmography (PPG) signals from one or more PPG sensors of a monitoring apparatus, the PPG signals being generated based upon optically detecting pulsed variations in blood flow. Block 132 comprises obtaining a motion sensor signal from a motion sensor in the monitoring apparatus. Block 134 comprises identifying, based upon the motion sensor signal, one or more periods of motion of the monitoring apparatus. Block 136 comprises selectively obtaining and storing segments of the PPG signals based on a temporal relationship between the segments of the PPG signals and the identified periods of motion.

In an embodiment, the temporal relationship indicates that the selectively obtained and stored segments of the PPG signals do not correspond to the identified periods of motion. In an embodiment, control program 124 may be programmed to cause generating and storing, based upon the segments of the PPG signals, PPG waveform data identifying waveform characteristics associated with the PPG signals, and generating and storing, based on the PPG waveform data, arrhythmia event data describing one or more arrhythmia events. The PPG waveform data can include a peak-to-peak dataset comprising one or more interval values representing time intervals between one or more successive peaks in the PPG signals. Additionally or alternatively, the PPG waveform data includes an amplitude dataset comprising one or more amplitude values associated with one or more peaks in the PPG signals. The arrhythmia event data may describe one or more arrhythmia types and arrhythmia durations that are associated with the one or more arrhythmia types.

In one approach, the system is programmed to cause comparing a motion-related metric generated based upon the motion sensor signal to a specified motion threshold value; determining, based on the comparing, that the one or more periods of motion indicate low motion; and determining and storing one or more arrhythmia types and arrhythmia durations that are associated with the one or more arrhythmia types only during the one or more periods of motion that indicate low motion. The system also may be programmed to cause comparing a motion-related metric generated based upon the motion sensor signal to a specified motion threshold value; determining, based on the comparing, that the one or more periods of motion indicate sleep, and determining and storing one or more arrhythmia types and arrhythmia durations that are associated with the one or more arrhythmia types only during the one or more periods of motion that indicate sleep. Or, the system may be programmed to cause comparing a motion-related metric generated based upon the motion sensor signal to a specified motion threshold value; determining, based on the comparing, that the one or more periods of motion indicate high motion; and in response thereto, determining and storing one or more arrhythmia types and arrhythmia durations that are associated with the one or more arrhythmia types only during additional time periods that do not correspond to the one or more periods of motion that indicate high motion.

As one example of arrhythmia detection, the system may be programmed for detecting one or more low amplitude PPG signals in the PPG signals, and in response thereto, classifying a portion of the PPG signals corresponding to the low amplitude PPG signals as representing an arrhythmia.

A feedback loop from block 109 to other functions or routines of the control program 124 may be implemented for purposes of changing operation of the control program in response to the characteristics that have been detected. For example, feedback specifying a classification or characterization of the PPG data as arrhythmia, from block 109, may cause the control program to begin transmitting data to host computer 110 at higher temporal resolution or frequency when the control program 124 detects signs of AF or arrhythmias.

Alternatively, the control program 124 may be configured for comparing a motion-related metric generated based upon the motion sensor signal to a specified motion threshold value; determining, based upon the comparing, that the one or more periods of motion indicate exercise, and in response thereto, determining and storing one or more arrhythmia types and arrhythmia durations that are associated with the one or more arrhythmia types only during additional time periods that do not correspond to the one or more periods of motion that indicate exercise. One feature of this approach may include, before the determining that the one or more periods of motion indicate exercise, obtaining the PPG signals at a first temporal resolution, and determining, based upon the motion sensor signal, that the one or more periods of motion indicating exercise have ended and are followed by one or more periods of low motion, and in response thereto, modifying a temporal resolution configuration parameter of the monitoring apparatus to cause the PPG signals associated with the one or more periods of low motion to be obtained at a second temporal resolution that is higher than the first temporal resolution. The control program 124 also could be configured for classifying, based on the obtained PPG signals associated with the one or more periods of low motion, a portion of the PPG signals as representing success or failure in a clinical stress test. Or, the control program 124 may be configured to perform determining, based upon the motion sensor signal, that the one or more periods of motion indicating exercise have ended and are followed by one or more periods of low motion, and in response thereto, determining and storing one or more arrhythmia types and arrhythmia durations that are associated with the one or more arrhythmia types during the one or more periods of low motion that follow the one or more periods of motion indicating exercise. If the system detects one or more arrhythmias during the one or more periods of low motion that follow the one or more periods of motion indicating exercise, the system may classify a corresponding portion of the PPG signals (associated with the one or more periods of low motion) as a failure of a clinical stress test.

As another example, the control program 124 may be configured for comparing a motion-related metric generated based upon the motion sensor signal to a specified motion threshold value; determining, based upon the comparing, that the one or more periods of motion indicate exercise, and in response thereto, identifying an instance of chronotropic incompetence, based on one or more heart rate values measured during the one or more periods of motion that indicate exercise.

FIG. 1C illustrates an example process of dynamically changing the temporal frequency at which PPG data is obtained in response to detecting an arrhythmia event. In one embodiment, FIG. 1C may serve as an algorithm that may be used as a basis for programming instructions for control program 124. In one embodiment, a method or algorithm comprises obtaining one or more photoplethysmography (PPG) signals from one or more PPG sensors of a monitoring apparatus at a first temporal resolution, the PPG signals being generated based upon optically detecting pulsed variations in blood flow, as seen at block 140. At block 142, the process is configured for generating and storing, based upon the PPG signals, a PPG waveform dataset identifying waveform characteristics associated with the PPG signals. At block 144, the process is configured for detecting, based upon the PPG waveform dataset, one or more cardiac arrhythmia events. At block 146, in response to detecting, based on the PPG waveform dataset, the one or more cardiac arrhythmia events, the process modifies a temporal resolution configuration parameter of the monitoring apparatus to cause the PPG signals to be received at a second temporal resolution that is higher than the first temporal resolution.

In such an embodiment, the cardiac arrhythmia events comprise any one or more of cardiac chronotropic incompetence, tachycardia, bradycardia, atrial fibrillation or other cardiac arrhythmia. The approach may further comprise, based upon the PPG waveform dataset, determining and storing one or more cardiac arrhythmia datasets representing, for each of the cardiac arrhythmia events, a type and a duration associated with the cardiac arrhythmia event. In yet another feature of the approach of FIG. 1C, the method may comprise generating, based upon the PPG signals of the second temporal resolution, a second PPG waveform dataset identifying additional waveform characteristics associated with the PPG signals of the second temporal resolution; and based upon the second PPG waveform dataset, determining and storing one or more high resolution cardiac arrhythmia datasets representing one or more cardiac arrhythmia types and durations associated with the types. In a related feature of the approach of FIG. 1C, the method may comprise periodically transferring one or more of the PPG signals of the second temporal resolution, the second PPG waveform dataset or the one or more high resolution cardiac arrhythmia datasets from the monitoring apparatus to a server computer using a wireless communication link; receiving, at the server computer, a call to an application programming interface (API) of the server computer that requests one or more of the PPG signals of the second temporal resolution, the second PPG waveform dataset or the one or more high resolution cardiac arrhythmia datasets; and in response to the call, transmitting, from the server computer to a host computer that transmitted the call, one or more of the PPG signals of the second temporal resolution, the second PPG waveform dataset or the one or more high resolution cardiac arrhythmia datasets.

In a further feature of the approach of FIG. 1C, the method may comprise using the server computer, generating one or more output metrics based upon one or more of the PPG signals of the second temporal resolution, the second PPG waveform dataset or the one or more high resolution cardiac arrhythmia datasets; receiving, at the server computer, a call to an application programming interface (API) of the server computer that requests one or more of the output metrics; and in response to the call, transmitting, from the server computer to a host computer that transmitted the call, one or more of the output metrics.

Any of these approaches relating to the method of FIG. 1C may further comprise receiving a motion sensor signal from a motion sensor in the monitoring apparatus; identifying, based upon the motion sensor signal, one or more periods of motion of the monitoring apparatus; and excluding cardiac data associated with the periods of motion from the PPG signals of the second temporal resolution, the second PPG waveform dataset, or the one or more high resolution cardiac arrhythmia datasets. The process may be programmed for generating, as the output metrics, one or more data values representing heartbeats, heartbeat sequences, number of abnormal heartbeat sequences, number of arrhythmia events, or type of arrhythmia events. The approach may further comprise determining, based on the PPG waveform dataset, that the one or more cardiac arrhythmia events have concluded; and modifying the temporal resolution configuration parameter of the monitoring apparatus to cause the PPG signals to be received at the first temporal resolution.

An example of a standard frequency of data collection is 25 Hz, and an example of higher resolution is 100 Hz, but other embodiments may use other frequencies. Higher temporal resolution of PPG can allow the extraction of high fidelity morphological features which can then lead to more accurate classification of PPG segments that constitute arrhythmic event candidates. Detection of an elevated heart rate as a characteristic at block 109 also could trigger a change in the frequency of data collection under control of the control program 124. In one embodiment, detection of an arrhythmia event at block 109 may cause a change in the amount of data collected, or both the frequency and the range. For example, for some arrhythmia events, capturing data surrounding the event may be useful. To address this, the control program 124 may implement algorithms, functions or routines for detecting short-term arrhythmia events and, in response, storing or transmitting PPG data that is obtained around such events. In one embodiment, the control program 124 may be configured or programmed to cause continuously capturing the PPG data in a circular buffer; the size of such a buffer may vary in different embodiments and examples might be buffers that capture 10 seconds of data, 60 seconds of data, etc. In such an embodiment, if the system detects a possible arrhythmia event of interest at a given time, the system could move the contents of the buffer, representing PPG data obtained earlier than the event, to non-volatile storage, to other separate storage, or to a server computer by uploading. Additionally or alternatively, the system could change the data collection frequency in response to the event, so that the buffer is subsequently stored with high frequency data, and then upload, separately store, or otherwise process the high frequency data that was obtained after the event. Further, the control program 124 may use feedback from block 109 for tracking periods of sleep using a motion sensor to measure a drop in heart rate during sleep, or to trigger higher frequency data collection for purposes of assessing sleep apnea, as further described herein.

To further increase the robustness of PP estimation, erroneous PP pulses can be detected by calculating one or more morphological features from the pulse, such as maximum & minimum amplitude, maximum and minimum slope, area, or width, and comparing these features with the same features obtained from neighboring pulses, or averaged values of the same features obtained from neighboring pulses. If the comparison yields large relative differences, then the pulse can be discarded.

Additionally or alternatively, with respect to characterizing rhythm at block 109, other output metrics may be generated as seen at block 112. For example, during periods of sleep and stillness, block 112 can comprise generating and outputting values for output metrics such as number of ventricular beats, number of two beat sequences ("bigeminy"), number of three beat sequences ("trigemini"), or others.

In various embodiments, all or part of blocks 105, 107, 109, 112 may be implemented using software or firmware that is hosted by and executed using the activity monitoring device 101 or the host computer 110. For example, the activity monitoring device 101 may be configured or programmed to obtain the motion sensor signal 102 and the PPG signal 103, and to periodically upload data representing these signals via one or more networks 108 to the host computer 110, and the host computer then may perform one or more of blocks 105, 107, 109, 112 in the manner described herein. Uploading may occur continuously, at particular times as specified in a schedule, or in response to specified events such as approaching or reaching a maximum storage capacity of memory in the activity monitoring device 101. Or, the activity monitoring device 101 may perform one or more of blocks 105, 107, 109, 112, and may provide a display at the device of the output of block 109 or block 112 or both. Additionally or alternatively, the activity monitoring device may perform one or more of blocks 105, 107, 109, 112, and may upload or otherwise provide output data resulting from block 109 or block 112 to the host computer 110 for further analysis, reporting, logging or other use. Uploading may involve transferring data in the form as originally collected at the activity monitoring device 101, or compression techniques may be used to compress the data prior to transfer.

In an embodiment, the host computer 110 may implement an application programming interface (API) to permit third party server computers or applications to send API calls and to receive responses comprising any of the data that the host computer has collected or formed using the processes described above.

Figure 1D:
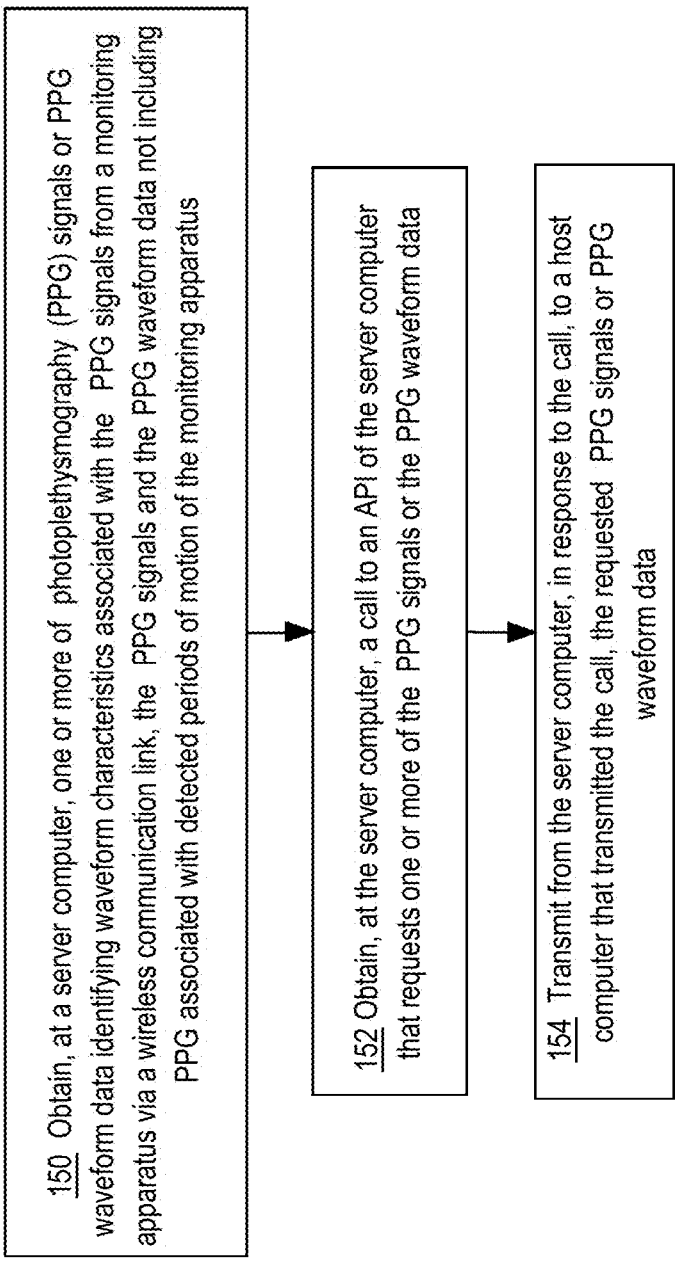
FIG. 1D illustrates an example method of providing PPG signal data or PPG waveform data using an API.

FIG. 1D illustrates an example method of providing PPG signal data or PPG waveform data using an API. In an embodiment, FIG. 1D may serve as an algorithm that may be used as a basis for programming instructions for control program 124. In one embodiment, at block 150, the process performs obtaining, at a server computer, one or more of photoplethysmography (PPG) signals or PPG waveform data identifying waveform characteristics associated with the PPG signals from a monitoring apparatus via a wireless communication link, the PPG signals and the PPG waveform data not including PPG data associated with detected periods of motion of the monitoring apparatus. At block 152, the process is configured for obtaining, at the server computer, a call to an application programming interface (API) of the server computer that requests one or more of the PPG signals or the PPG waveform data. At block 154, the process is configured for transmitting from the server computer, in response to the call, to a host computer that transmitted the call, the requested PPG signals or PPG waveform data.

One feature of this approach may include, using the server computer, generating and storing one or more output metrics based upon one or more of the PPG signals or the PPG waveform data; obtaining, at the server computer, a call to the application programming interface (API) of the server computer that requests one or more of the output metrics; and in response to the call, transmitting, from the server computer to a host computer that transmitted the call, the requested output metrics. The output metrics may comprise one or more data values representing heartbeats, heartbeat sequences, number of abnormal heartbeat sequences, number of arrhythmia events, or type of arrhythmia events.

In one embodiment, the detected periods of motion may be detected based on a motion sensor signal from an accelerometer in the monitoring apparatus. Further, in an embodiment, the monitoring apparatus obtains raw PPG data from one or more PPG sensors of the monitoring apparatus, and the monitoring apparatus selectively obtains, from the raw PPG data, the PPG signals not including PPG data associated with the detected periods of motion. For example, the activity monitoring device 101 may be programmed to determine periods of motion represented in the raw PPG data and to exclude periods of motion from the PPG signals that are uploaded to the host computer 110 and thereby become available via the API.

In other embodiments, various therapeutic methods may be performed based on the data and analysis described above. For example, embodiments encompass a method of providing a diagnosis of arrhythmia. Embodiments also encompass methods of recommending treatment using any of beta blockers, calcium channel blockers, digoxin, sodium channel blockers, potassium channel blockers or blood thinners such as anti-platelets and anti-coagulants.

Figure 1E:
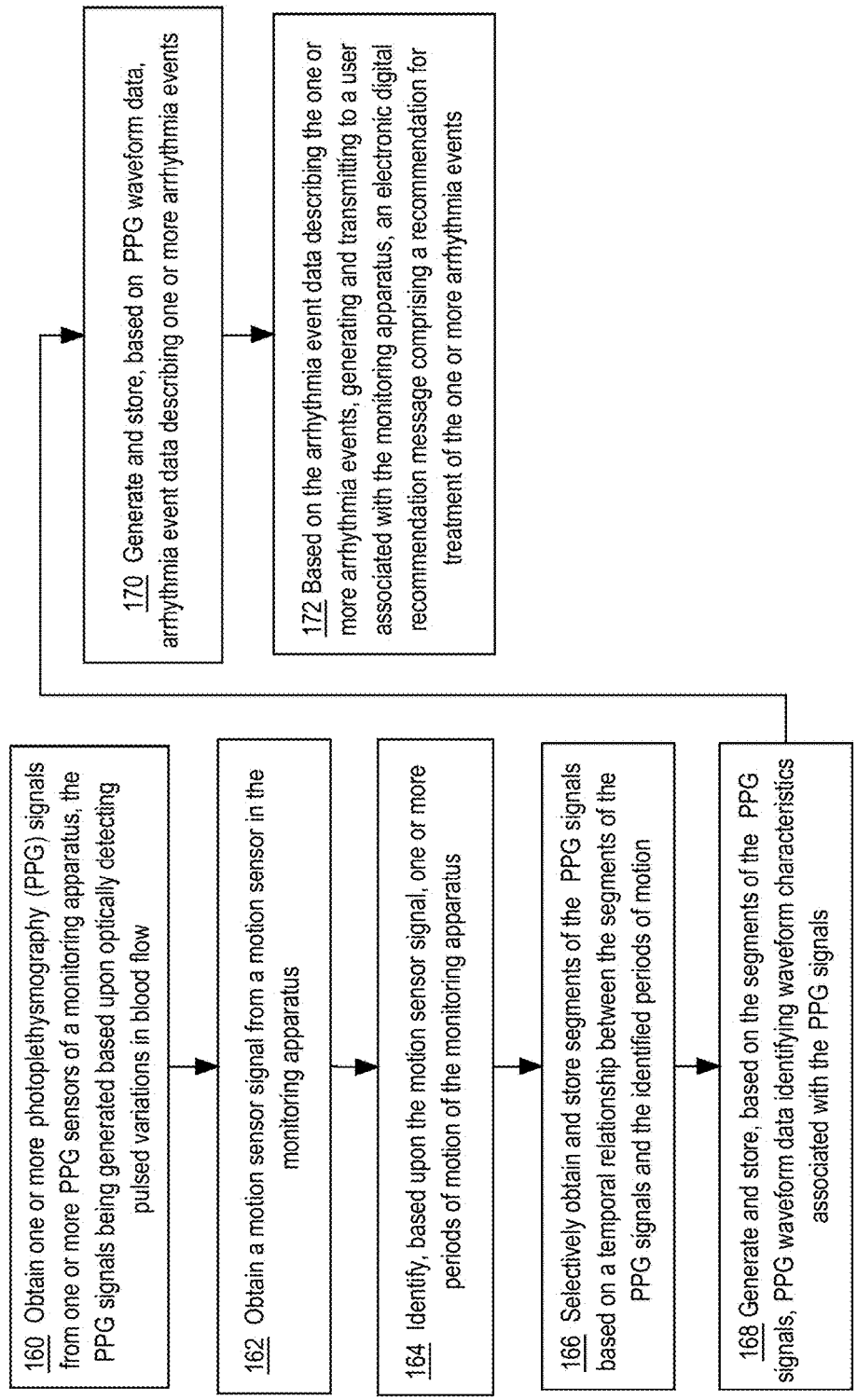
FIG. 1E illustrates an example method of treatment of the human body.

FIG. 1E illustrates an example method of treatment of the human body. In one embodiment, at block 160, the method comprises obtaining one or more photoplethysmography (PPG) signals from one or more PPG sensors of a monitoring apparatus, the PPG signals being generated based upon optically detecting pulsed variations in blood flow. At block 162, the process comprises obtaining a motion sensor signal from a motion sensor in the monitoring apparatus. At block 164, the process comprises identifying, based upon the motion sensor signal, one or more periods of motion of the monitoring apparatus. At block 166, the process comprises selectively obtaining and storing segments of the PPG signals based on a temporal relationship between the segments of the PPG signals and the identified periods of motion. At block 168, the process comprises generating and storing, based on the segments of the PPG signals, PPG waveform data identifying waveform characteristics associated with the PPG signals. At block 170, the process comprises generating and storing, based on PPG waveform data, arrhythmia event data describing one or more arrhythmia events. At block 172, the process comprises, based on the arrhythmia event data describing the one or more arrhythmia events, generating and transmitting to a user associated with the monitoring apparatus, an electronic digital recommendation message comprising a recommendation for treatment of the one or more arrhythmia events.

Classifying rhythm types at block 109 may, in one embodiment, provide data useful as input in generating a treatment plan for a patient, as seen at block 114. In such an embodiment, block 114 may comprise performing various therapeutic methods based on the data and analysis described above. For example, embodiments encompass a method of providing a diagnosis of arrhythmia. Embodiments also encompass methods of recommending treatment using any of beta blockers, calcium channel blockers, digoxin, sodium channel blockers, potassium channel blockers or blood thinners such as anti-platelets and anti-coagulants. When block 109 indicates bradycardia, then the treatment plan formed at block 114 may comprise implanting a pacemaker. When block 109 indicates AF, the treatment plan created at block 114 may comprise treatment by medication or a procedure to cardiovert the heart. In any of these embodiments, block 114 may comprise, based on arrhythmia event data generated at block 109 and describing one or more arrhythmia events, generating and transmitting to a user associated with the monitoring apparatus, an electronic digital recommendation message comprising a recommendation for treatment of the one or more arrhythmia events, and comprising any one or more of the treatment plans or recommendations described above.

Embodiments recognize that information about cardiac rhythm also can be reflected in values of the amplitude of the PPG signal 103. For example, a premature atrial contraction may result in a less effective beat, so that the volume of blood passing under the PPG sensor is reduced, thereby causing a lower amplitude signal. In an embodiment, the activity monitoring device 101 or host computer 110 are configured or programmed to perform, as part of block 109, detection of low amplitude datasets of the PPG signal 103. In one embodiment, the activity monitoring device 101 or host computer 110 is configured or programmed to compare each peak signal value detected in the PPG signal to a stored threshold value indicating a minimum amplitude value that is associated with normal rhythm. If a particular peak is below the threshold value, then in response, the activity monitoring device 101 or host computer 110 may store a record identifying a point at which a low amplitude peak value was detected. The record may include, for example, data identifying the PPG signal, a tag or type value signifying low amplitude, and a timestamp or sequence number indicating a position within the entire PPG signal dataset at which the low amplitude peak is found.

In an embodiment, activity monitoring device 101 or host computer 110 is configured or programmed to detect premature ventricular contraction (PVC). For example, activity monitoring device 101 or host computer 110 is configured or programmed to compute and store an area value representing the area under the PPG curve, and in response, to compare the area value to a stored threshold area value associated with PVC and/or to stored area values associated with the preceding N heartbeats, where 1<=N<=10. Such embodiments recognize that a PVC may be manifest as one or more signals having higher amplitude and area compared to the last two or three normal beats preceding the PVC.

In an embodiment, activity monitoring device 101 or host computer 110 is configured or programmed to detect periods of sleep apnea. In one example embodiment, the activity monitoring device 101 or host computer 110 is configured or programmed to detect bradycardia or tachycardia patterns at timescales that are consistent with apnea events. For example, in one embodiment, the activity monitoring device 101 or host computer 110 is configured or programmed to inspect values of the PPG signal 103 over a specified time period, such as 20 to 30 seconds, to identify periods of bradycardia or tachycardia. Template matching may be used for this purpose.

In an embodiment, activity monitoring device 101 or host computer 110 is configured or programmed to detect other forms of arrhythmia, as further described. For example, control program 124 may be configured to obtain PPG signals and a motion sensor signal as previously described and to perform, based upon the motion sensor signal, detecting a period of low motion of the apparatus consistent with sleep of a user over a specified time sufficient to permit detection of sleep apnea; detecting, based on the PPG signals, an indication of bradycardia; and in response thereto, marking a portion of the PPG signals corresponding to the period of low motion as representing bradycardia. A portion of the PPG signals may be marked as representing sleep apnea. Further, the control program 124 may be configured to perform, based upon the motion sensor signal, detecting a period of low motion of the apparatus consistent with sleep of a user over a specified time sufficient to permit detection of sleep apnea; detecting, based on the PPG signals, an indication of tachycardia; and in response thereto, marking a portion of the PPG signals corresponding to the period of low motion as representing tachycardia. This approach also may include marking the portion of the PPG signals as representing sleep apnea.

Additionally or alternatively, the system may be programmed to perform, based upon the motion sensor signal, detecting a period of low motion of the apparatus consistent with sleep of a user; detecting, based on the PPG signals, a drop in heart rate during the period of low motion consistent with sleep; and generating and storing, based on a portion of the PPG signals not associated with the period of low motion consistent with sleep, and the drop in heart rate during the period of low motion consistent with sleep, an estimate of heart rate variability.

The system may be programmed as part of block 109 to perform classifying, based on the PPG signals, a portion of the PPG signals as representing atrial fibrillation. Additionally, block 109 may include generating and storing, in association with the portion of the PPG signals representing atrial fibrillation, values specifying an amount and duration of atrial fibrillation. Classifying signals at block 109 also may be integrated in an approach comprising obtaining the PPG signals at a first temporal resolution; and in response to detecting, based on the PPG signals, any one or more of cardiac chronotropic incompetence, cardiac arrhythmia, tachycardia, bradycardia, or atrial fibrillation, performing one or more of modifying a temporal resolution configuration parameter of the monitoring apparatus to cause the PPG signals to be obtained at a second temporal resolution that is higher than the first temporal resolution; or outputting an alert signal.

Figure 1F:
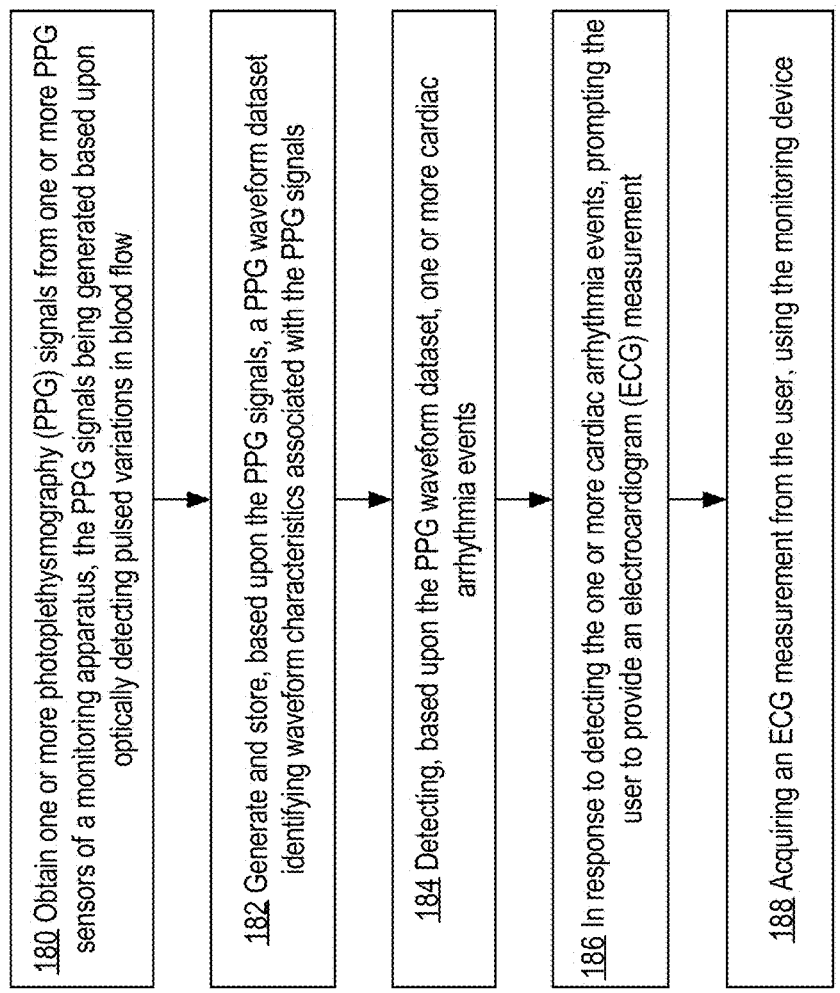
FIG. 1F illustrates an example process of acquiring an electrocardiogram measurement in response to detecting an arrhythmia event.

FIG. 1F illustrates an example process of acquiring an electrocardiogram (ECG or EKG) measurement in response to detecting an arrhythmia event. In one embodiment, FIG. 1F may serve as an algorithm that may be used as a basis for programming instructions for control program 124. In one embodiment, a method or algorithm comprises obtaining one or more photoplethysmography (PPG) signals from one or more PPG sensors of a monitoring apparatus, the PPG signals being generated based upon optically detecting pulsed variations in blood flow, as seen at block 180. At block 182, the process is configured for generating and storing, based upon the PPG signals, a PPG waveform dataset identifying waveform characteristics associated with the PPG signals. At block 184, the process is configured for detecting, based upon the PPG waveform dataset, one or more cardiac arrhythmia events. In such an embodiment, the cardiac arrhythmia events comprise any one or more of cardiac chronotropic incompetence, tachycardia, bradycardia, atrial fibrillation or other cardiac arrhythmia. At block 186, in response to detecting the one or more cardiac arrhythmia events, the process is configured to prompt the user to provide an ECG measurement. For example, the process may generate one or more alert signals, messages or notifications as output to the activity monitoring device 101 or host computer 110. The process thus notifies the user of the need to provide an ECG measurement.

At block 188, the process acquires an ECG measurement from the user, using the activity monitoring device 101. In one embodiment, activity monitoring device 101 comprises one or more sensors for taking an ECG measurement. For example, activity monitoring device 101 may be a wearable wrist-based device that includes a first electrical sensor positioned under the device (e.g., on the side of the device facing the user's wrist) with a contact point that contacts the wrist of the hand that is wearing activity monitoring device 101. Activity monitoring device 101 may further comprise a second electrical sensor, separate from the first electrical sensor. For example, the second electrical sensor may be positioned on the top of device and may provide a contact point for a finger from the opposing hand of the user. Thus, a user can contact the first electrical sensor using the wrist of the hand wearing the activity monitoring device 101, and the user can contact the second electrical sensor using a finger of the opposing hand, thereby creating an electrical circuit that can be used for obtaining a differential ECG signal. The process thus uses PPG signals to identify an appropriate time for acquiring an ECG measurement from the user. FIG. 2 is a graph 200 of an example cardiac arrhythmia caused by premature atrial contractions. Arrows 201-204 indicate beats resulting from anomalous contraction of the atrium before the normal pacemaker signal. In this condition, a beat happens earlier than intended. Usually the following beat is longer to compensate for this, as the ventricle repolarizes, a condition indicated by an SA reset signal 205 in the dataset.

Figure 3:
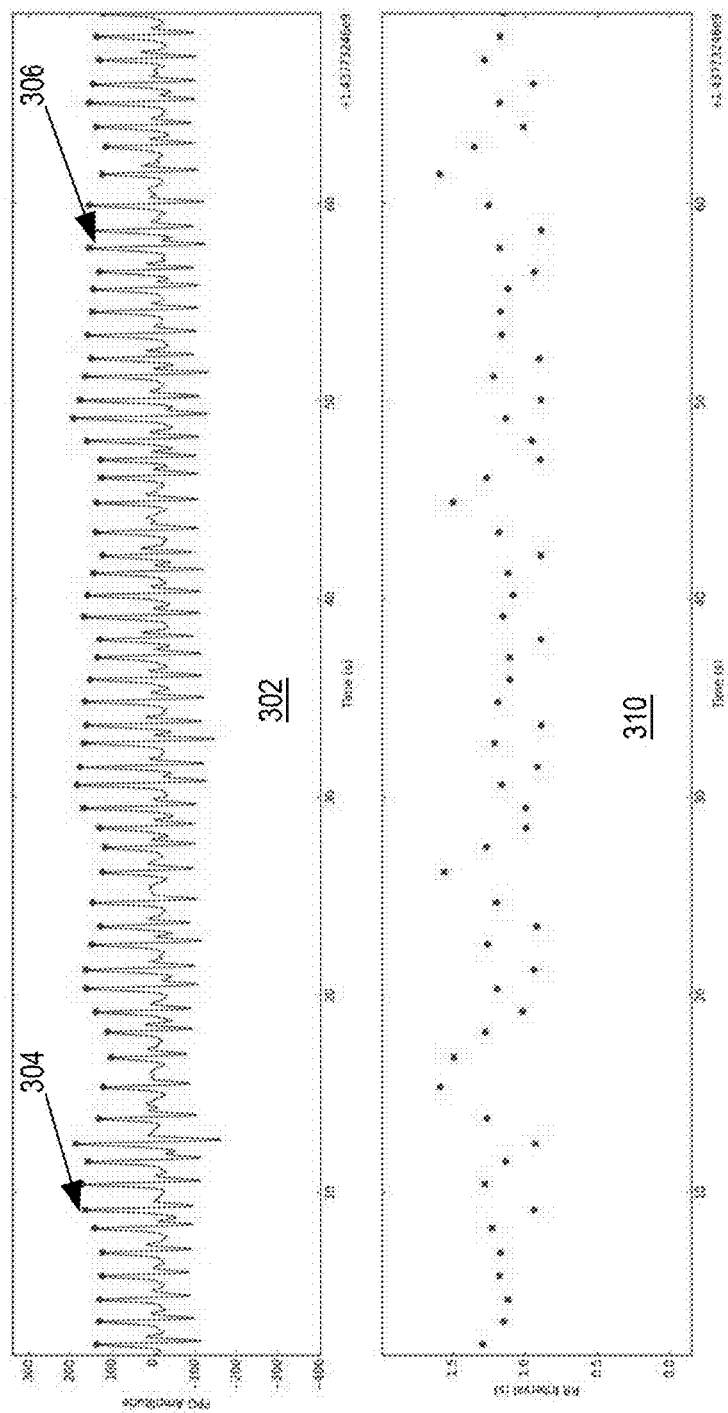
FIG. 3 illustrates two graphs providing an example of data analysis that may be used to detect premature atrial contraction.

FIG. 3 illustrates two graphs providing an example of data analysis that may be used to detect premature atrial contraction. Graph 302 illustrates the amplitude of PPG signals 103 on the vertical axis as compared to time represented in the horizontal axis. Arrows 304, 306 indicate premature atrial contraction. Graph 310 illustrates running average values extracted from the data shown in graph 302. Based on the running average values, incidents of low amplitude suggesting premature atrial contraction may be rapidly identified as they are outliers in the data of graph 310. In either the activity monitoring device 101 or the host computer 110, rules for detecting premature atrial contractions can be programmed using the relationship If $RR[n]<0.9\times RR_{running\_average}$ AND $RR[n+1]>1.1*RR[n]$, then $RR[n]$ is a PAC where $RR_{running\_average}$ is a running average of the RR intervals over a specified number of beats, such as the last 10 beats.

Figure 4:
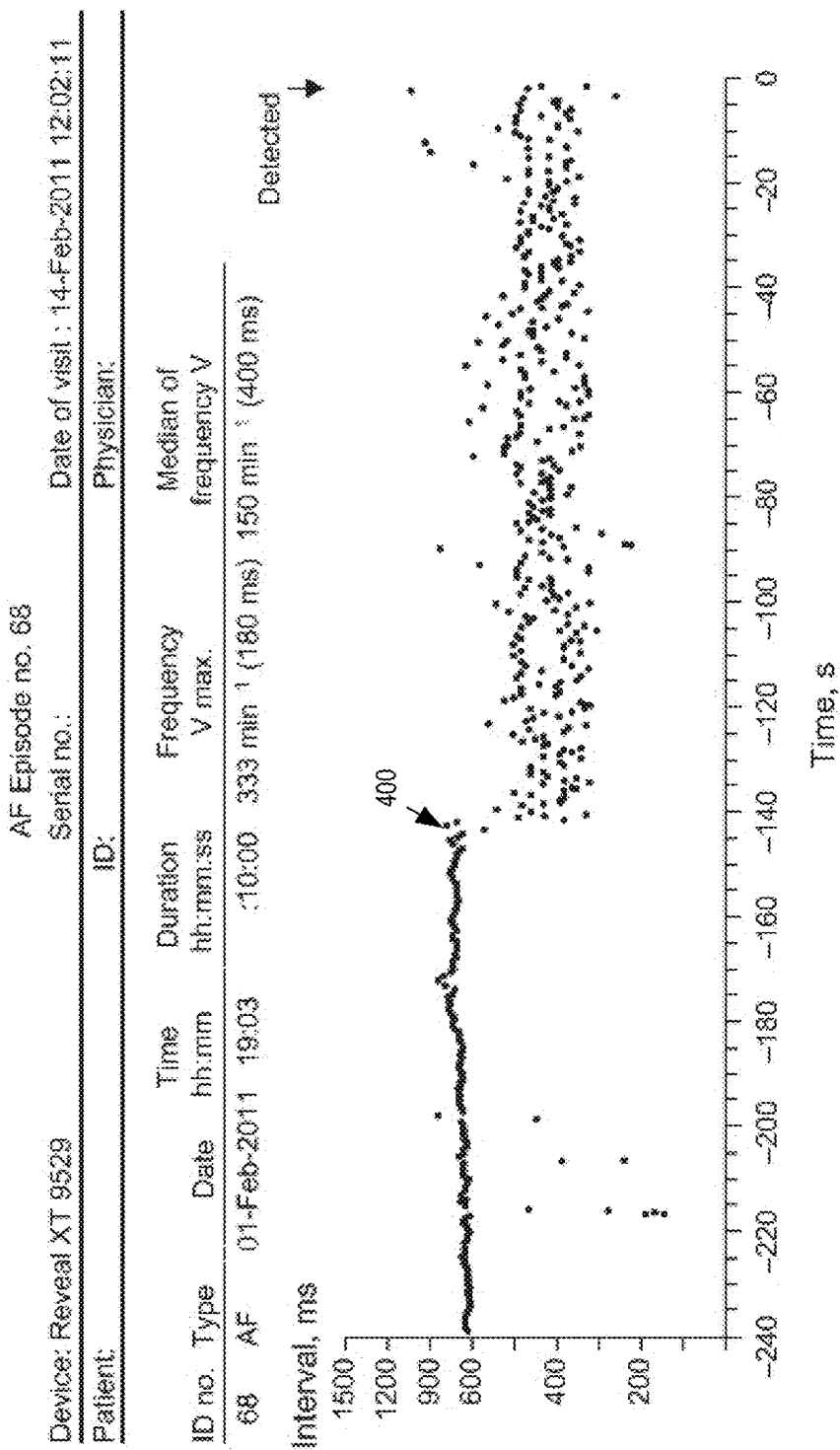
FIG. 4 illustrates a graph of an RR interval series associated with atrial fibrillation when a person converts from normal sinus rhythm to AF.

FIG. 4 illustrates a graph 400 of an RR interval series associated with atrial fibrillation when a person converts from normal sinus rhythm to AF. Embodiments recognize that in AF, the heart rate is typically elevated, and also "disorganized". In an embodiment, activity monitoring device 101 or host computer 110 is configured or programmed to detect peaks of the PPG intervals and to perform pattern analysis to identify elevated heart rate and disorganized beat activity. In response to detecting both elevated rate and disorganized activity, activity monitoring device 101 or host computer 110 is configured or programmed to store a record identifying a point at which AF was detected. The record may include, for example, data identifying the PPG signal, a tag or type value signifying AF, a timestamp or sequence number indicating a position within the entire PPG signal dataset at which the AF was found, and a duration of the AF.

2. Example Implementation for Detecting Atrial Fibrillation 2.1 the Root Mean Square of Successive Differences ("RMSSD") Approach The data processing system described thus far, using either activity monitoring device 101 or host computer 110 or both, provides a set of PP interbeat intervals. One of the most common arrhythmias is atrial fibrillation, whose prevalence increases with age, so that an estimated 10% of the 80-89 year age group suffer from this condition. It increases the risk of stroke significantly as blood clots can form in the atria, due to the inefficient pumping of the atria in AF. AF can either be chronic (permanent) or intermittent (referred to as paroxysmal AF). The system described herein may be configured or programmed for determining either type.

Figure 5:
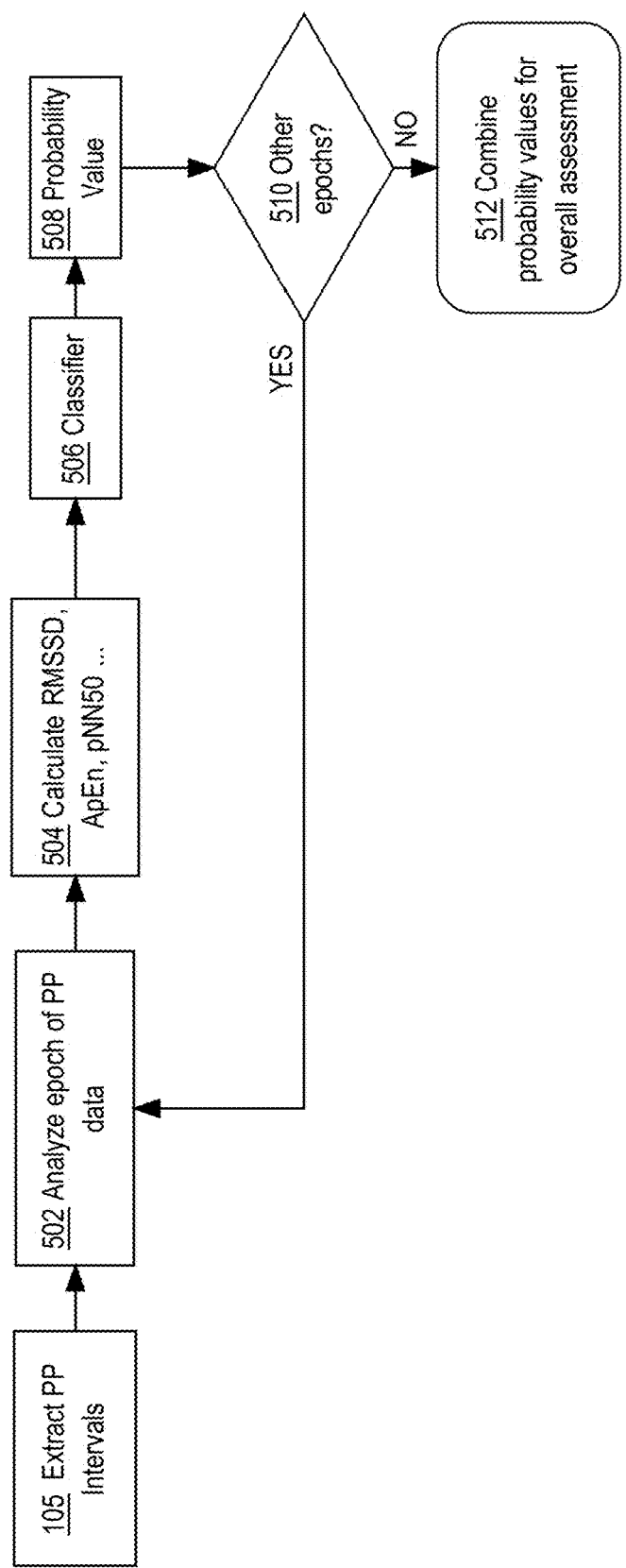
FIG. 5 illustrates data flow and processing steps in one embodiment that is configured to characterize atrial fibrillation.

FIG. 5 illustrates data flow and processing steps in one embodiment that is configured to characterize atrial fibrillation. PP interval data obtained at block 105, as previously described for FIG. 1A. In an embodiment, the PP interval data defines a set of times at which PP events occurred. The PP interval data may be divided as seen at block 502 into segments or epochs of fixed duration which are long enough to contain multiple beats, but short enough that short episodes of AF will not be swamped by the overall record. The particular time duration for an epoch is not critical, but 5 minutes of data is a workable example.

At block 504, values for the following parameters are determined for each epoch (e.g., 5 minute period of data):

The Root Mean Square of Successive Differences (RMSSD) (the square root of the mean of the squares of the successive differences between adjacent intervals);

NN50 (the number of PP intervals that differ by more than 50 ms, as a percentage of the overall number of beats);

The approximate entropy (ApEn) of the series.

Values for these parameters have been found useful to characterize the increased irregularity of the cardiac rhythm during atrial fibrillation. Other metrics that could be used are the HF/LF ratio in the spectral domain, the standard deviation of the PP intervals, and others.

Values for these parameters are provided to a classifier 506, which has previously been trained on known sequences which contain AF and non-AF intervals. The output of the classifier stage may be a label for the epoch, indicating the presence of AF or non-AF, and a probability value 508 indicating the likelihood that AF is present in the epoch. Probability values may, in some embodiments, be generated as real number values between 0 and 1.

At block 510, the process determines whether other epochs are present in the extracted PP interval data, that is, whether other data remains to be evaluated. Individual epochs represented in the PP interval data can be non-overlapping or partially overlap. If the test of block 510 is true, then control may transfer back to block 502 to repeat the foregoing process for another epoch represented in the data.

If no other epochs remain in the data, then control transfers to block 512 at which an overall assessment can be made by assessing output from multiple epochs. In some embodiments, the system may be programmed to use a user probability value from one epoch to influence a combined output for multiple epochs. For example, if the probability value for a particular epoch is 0.51, but probability values for the surrounding epochs are lower to indicate non-AF, then the final labeling of the particular epoch may be set to non-AF also as it may represent a random artifact.

The classifier 506 in various embodiments can be a linear discriminant classifier, a quadratic discriminant classifier, a random forest classifier, a decision tree, a support vector machine classifier, or a neural network classifier. The parameters used by the classifier can be trained using PP intervals that have been obtained from subjects with known AF conditions; the presence of a known AF condition can be confirmed by simultaneous recording of an ECG on the same subject, plus visual inspection by an expert electrophysiologist, for example. Using this approach, the classifier will recognize periods of AF with a high degree of confidence.

2.2 Assessment of Correlated Sympathetic or Parasympathetic Activity

In an embodiment, the process described for FIG. 5 may be programmed or configured to first determine whether subjects have correlated sympathetic or parasympathetic activity, as that can change the pattern of irregularity shown in the PP sequence. In one embodiment, the system is configured or programmed to consider periods of the PP interval data. An example period is 60 minutes of data but other periods may be used in other embodiments. The period is divided into smaller segments, such as epochs of 5 minutes. The interval based power spectrum can be taken of the interval sequence in these smaller epochs to produce a power spectrum value S(f) where f is in units of cycles/interval.

As a basis for the power spectrum value, the system is programmed or configured to calculate a low-frequency band and a high frequency band of heart rate variability, for example, by integrating the spectral power over the range 0.04-0.15 cycles/interval for the LF power, and from 0.15-0.4 cycles/interval for the HF power. When a 60-minute period of data is used, the foregoing process yields 12 HF estimate values and 12 LF estimate values. The system is configured or programmed to determine a correlation coefficient between the sets of estimate values. If a resulting correlation coefficient is high (e.g., >0.8), then the LF and HF are strongly correlated, indicating that the sympathetic and parasympathetic systems of the subject are well coupled.

Thereafter, the period of data can be divided into well-correlated versus not-well-correlated datasets, and different processing may be applied to each of the datasets. It has been empirically determined that the impact on the spectrum of AF is different for these groups.

Figure 6:
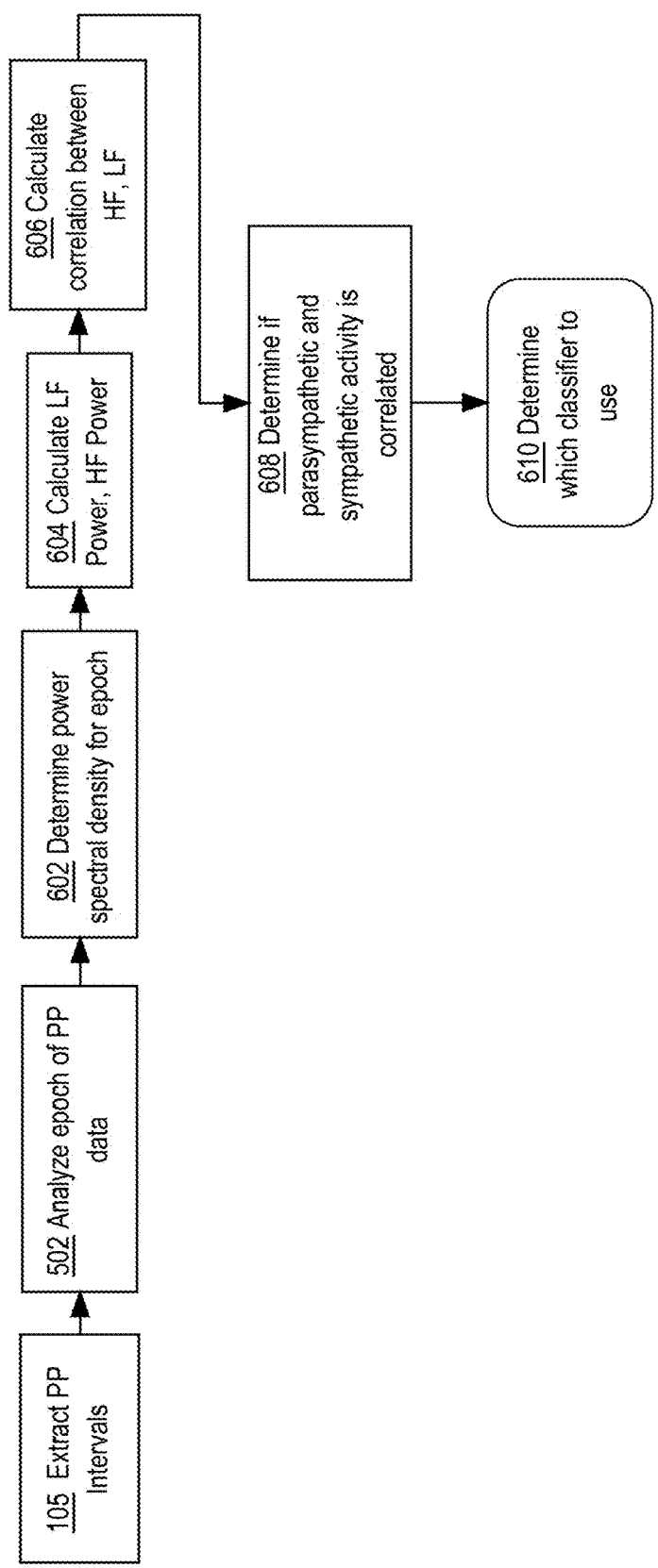
FIG. 6 illustrates data flow and processing steps in one embodiment that is configured to characterize atrial fibrillation in which correlated sympathetic or parasympathetic activity is considered.

FIG. 6 illustrates data flow and processing steps in one embodiment that is configured to characterize atrial fibrillation in which correlated sympathetic or parasympathetic activity is considered. As previously noted, natural physiological variability occurs in the rhythm dependent on how well coupled the sympathetic and parasympathetic activation is. In FIG. 6, blocks 105, 502 proceed as previously described for FIG. 5. At block 602, a power spectral density estimate value is determined for each epoch, which allows a power spectral density value of the epoch to be calculated. A High Frequency (HF) power value is obtained by integrating the power over 0.15-0.4 cycles/interval at block 604, and is deemed to reflect parasympathetic activation of the heart. The LF power is obtained by integrating the power over 0.04-0.15 cycles/interval, and reflects a mixture of sympathetic and parasympathetic activation. For some subjects, the sympathetic and parasympathetic activation will be highly correlated; therefore, a correlation is calculated at block 606 yielding a correlation coefficient which is tested at block 608 to determine whether a correlation appears to be present. Depending on the value of the correlation coefficient, at block 610, one of a plurality of different classifier models can be chosen from among those described above in connection with FIG. 5.

The classifier 504 of FIG. 5 then can be used as previously described to characterize an AF. Alternatively, the processing described herein to recognize abnormal beats can implemented in the classifier 504 of FIG. 5; for example, the classifier may be programmed to add in the number of abnormal beats observed in an minute epoch as a feature.

2.3 PPG Waveform Shape Analysis

Additionally or alternatively, the system may be programmed or configured to analyze the shape of the PPG waveform. This approach recognizes that characterizing AF may be improved by identifying premature atrial contractions ("PACs"), which comprise heart beats in which the electrical P-wave happens earlier in time than anticipated, due to an activation of the atria by an ectopic focus. Electrocardiogram (ECG) systems recognize PAC by abnormally shaped P waves, followed by a normal QRS complex. Because these atrial contractions are not under the control of the sinus node, they also give rise to a more erratic rhythm than is normally observed.

In an embodiment, the system is configured or programmed to recognize the possibility of a PAC occurrence by comparing the shape of the PPG pulses, and recognizing beats which are likely to be associated with a premature atrial contraction. In one embodiment, the comparing and recognizing comprise maintaining a periodically or continuously updated template of the expected pulse shape, and flagging any pulses which are significantly different (e.g., differing by more than a threshold amount or percentage) in shape, by comparing the current beat to the template. Various changes in the PPG shape could be caused by movement. Therefore, in one embodiment, the motion sensor signal 102 is used to decide if the activity monitoring device 101 is moving, or is within 5 seconds of movement, as one of the markers of PPG pulse shape. Accordingly, if the system identifies pulses that are significantly different in shape then the template, and if the motion sensor signal 102 indicates that the device 101 is moving or has moved within the last 5 seconds (e.g., by comparing a motion-related metric generated based on motion sensor signal 102 to a predetermined threshold value), then the given pulses will not be flagged as a possible PAC occurrence. Alternatively, if the system identifies pulses that are significantly different in shape then the template, and if the motion sensor signal 102 indicates that the device 101 is not moving and/or has not moved within the last 5 seconds (e.g., by comparing a motion-related metric generated based on the motion sensor signal 102 to a predetermined threshold value), then the given pulses will be flagged as a possible PAC occurrence.

Figure 8:
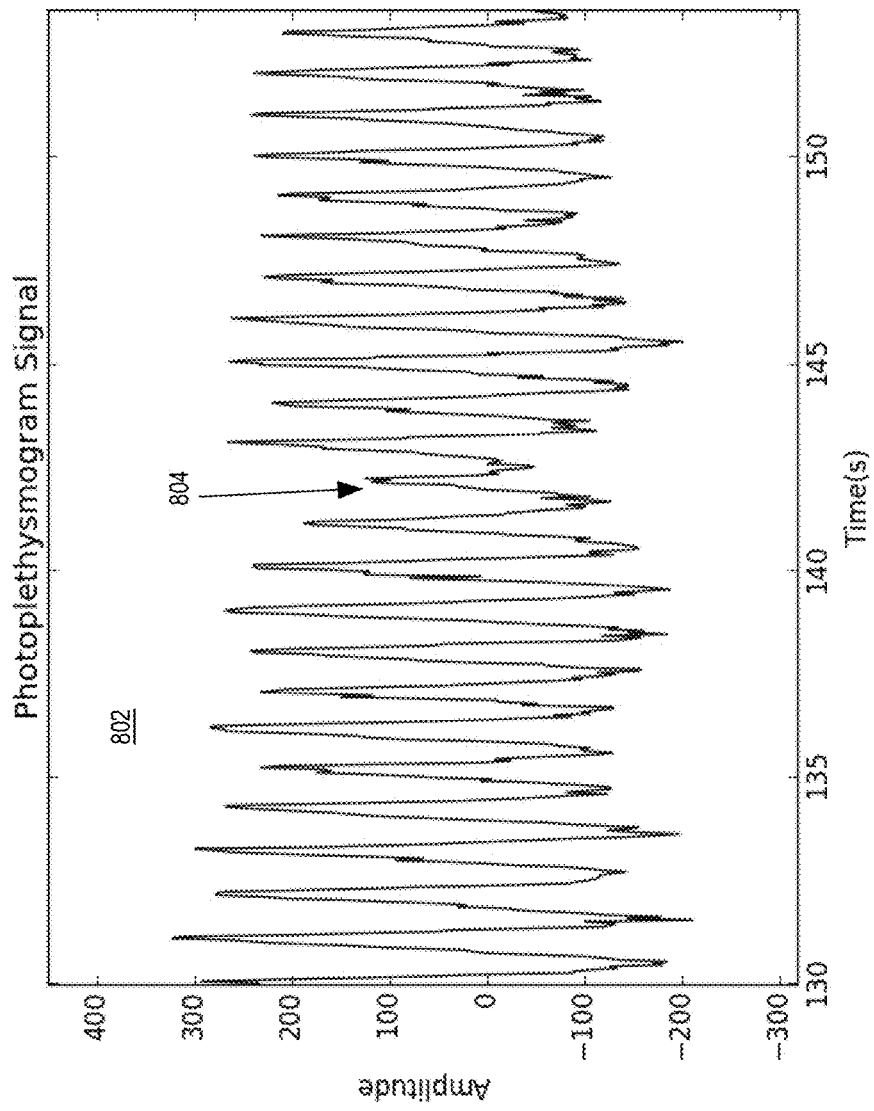
FIG. 8 illustrates an example dataset collected over approximately 25 seconds, in which each heart beat produces a distinctive peak.

FIG. 8 illustrates an example dataset collected over approximately 25 seconds, in which each heart beat produces a distinctive peak. As indicated by arrow 804 in graph 802, one beat differs significantly from its neighbors in amplitude and partially in shape, so it can be flagged as a potentially unusual beat. By comparing the beat at arrow 804 to templates of typical PAC beats, the beat at arrow 804 can be assigned a probability of being a PAC.

2.4 Integration with Mobile Computing and Cloud-Based Devices

Figure 7:
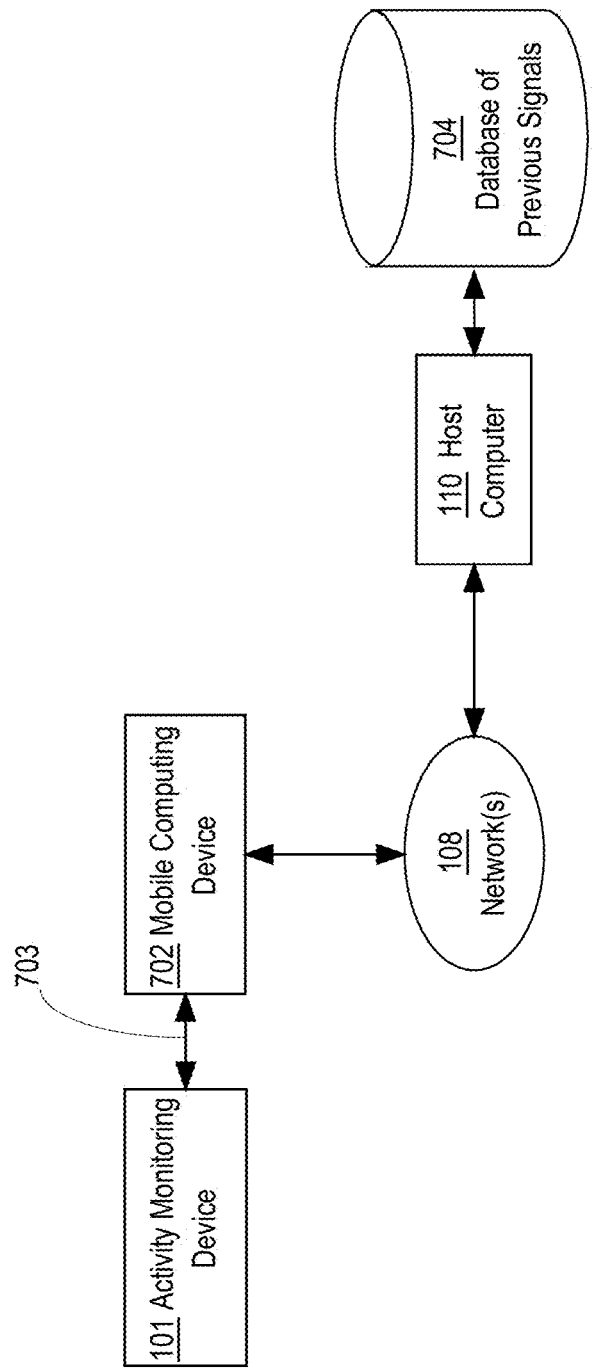
FIG. 7 illustrates a computer system in which an activity monitoring device is integrated with a mobile computing device.

The system described herein can be embedded in an ecosystem in which the activity monitoring device 101 can communicate with a mobile computing device using a wireless link, and the mobile computing device can perform further processing of the signal, or transmit the signals to a host computer such as a central server for analysis. FIG. 7 illustrates a computer system in which an activity monitoring device is integrated with a mobile computing device. In an embodiment, the activity monitoring device 101 communicates either raw data, or processed data to a mobile computing device 702, such as a smartphone, over a wireless link 703. Link 703 may use a short-range wireless communication protocol, such as Bluetooth, or near-field communication (NFC) protocols, WiFi or equivalents.

The mobile computing device 702 also can communicate with the activity monitoring device 101 to initiate recording data, instruct the device to record data at a higher sampling rate, give feedback to the user via vibration or audible or visual signals or displays, or to provide an interface to the user.

In an embodiment, mobile computing device 702 is configured to communicate via the cloud network(s) 108 with a host computer 110, which may comprise one or more server computers in any physical location or associated with a shared computing facility such as a virtualized cloud computing service. Host computer 110 can run more complex algorithms to recognize arrhythmias, as well as providing archiving and other communication functions. For example, a real-time notification system can comprise a server-executed algorithm that detects an unusual pattern (such as ventricular arrhythmias or other malignant arrhythmias, or any other types of arrhythmias or conditions described herein) and alerts a wearer of the activity monitoring device 101 or a medical caregiver associated with the wearer.

In an embodiment, host computer 110 is communicatively coupled to a database 704 of prior measurements. Host computer 110 may be programmed or configured to use the database 704 to compare the received signals to norms for a user subject, or with population norms. Using these approaches, specific rules for each user can be defined and stored for use under program control. An example programmed rule could comprise, generate an alert to a medical caregiver if a heart rate above 120 bpm is observed for more than 60 seconds. The database 704 also can store examples of irregular heart beat shapes and templates for use in the processes that have been previously described.

3. Characterization of Other Arrhythmias

The system can also be configured to recognize the following arrhythmias. The system can also decide to record heart rate under certain conditions, e.g., when the person is asleep or when the person is exercising, as these may be associated with certain phenomena.

BRADYCARDIA, which comprises a slower than normal heart rate. An example is less than 60 beats per minute (bpm), but the exact number depends on a user's age, gender and other values. In an embodiment, the system is programmed or configured to calculate heart rate by counting the number of beats in a defined period and to generate an alert or notification if the rate is below the defined threshold ATRIOVENTRICULAR (AV) BLOCK, which occurs when conduction from atria to ventricles is impaired. In an embodiment, AV block can be detected by identifying a long pause between successive PP beats. For example, a sequence of [0.8, 0.9, 0.8, 2.0, 0.8], where the numeric values indicate seconds between beats, might indicate an AV block.

VENTRICULAR TACHYCARDIA, which comprises a fast heartbeat caused by incorrect signaling in the ventricles. An example definition is heart rate of greater than 100 bpm, with at least three irregular heartbeats in a row. In an embodiment, the system may be programmed or configured to detect the irregular heartbeats based upon impact on the shape of the PPG waveform.

BIGEMINY, which is a particular arrhythmia in which a normal beat is followed by an abnormal beat, for example, a premature ventricular contraction. It can also be described as a continuous alteration of long and short beats. In an embodiment, the system may be programmed or configured to recognize bigeminy by calculating the autocorrelation of the PP intervals for time shifts of one and two beats, and identifying a non-correlation pattern or correlation pattern.

TRIGEMINY is a three-beat pattern comprising two normal beats followed by an extra beat, or one normal beat followed by two extra beats. In an embodiment, the system may be programmed or configured to recognize trigeminy by calculating the autocorrelation of the PP intervals for time shifts of one and two beats in a total of three or more beats, and identifying a non-correlation pattern or correlation pattern.

HRV ANOMALIES. Successive estimation of PP intervals allows for reliable estimation of Heart Rate Variability (HRV). Long term trends in HRV such as gradual decrease can be detected and can be used to trigger an alarm, as decreased HRV is correlated with poor cardiovascular outcomes and is a sign of autonomic imbalance.

SLEEP APNEA. A particular type of rhythm pattern is also associated with a condition called sleep apnea, in which the airflow of a person is either completely or partially obstructed due to collapse of their upper airway; this leads to a reduction in the oxygen level in the blood, which has a distinct effect on heart rate that is capable of observation in a subject. Oxygen desaturation leads to a reduction in heart rate (bradycardia) followed by a rapid increase in rate after recovery breaths bring air back into the lungs. Thus, for example, if a user's base heart rate is 70 bpm, a reduction to 60 bpm could occur in an apnea episode, followed by a recovery rate of 80 bpm, over a time period of 20-30 seconds.

Accordingly, in some embodiments, the activity monitoring device 101 or host computer 110 is configured or programmed to identify apnea events by detecting bradycardia and tachycardia patterns in specific sequences at timescales that are consistent with apnea events. For example, in one embodiment, the activity monitoring device 101 or host computer 110 is configured or programmed to inspect values of the PPG signal 103 over a specified time period, such as 20 to 30 seconds, to identify a period of bradycardia followed immediately by a period of tachycardia. Template matching may be used for this purpose. In some embodiments, control program 124 may be configured to obtain PPG signals and a motion sensor signal as previously described and to perform, based upon the motion sensor signal, detecting a period of low motion of the apparatus consistent with sleep of a user over a specified time sufficient to permit detection of sleep apnea; detecting, based on the PPG signals, an indication of bradycardia followed immediately by a period of tachycardia over a specified time period (such as 20 to 30 seconds); and in response thereto, marking a portion of the PPG signals corresponding to the period of low motion as representing bradycardia, tachycardia, and/or sleep apnea.

In an embodiment, patterns of change in heart rate associated with sleep apnea may be detected using programming or configuration to calculate the power spectral density estimate of the signal over fixed epochs of data, and then calculating the power in the band corresponding approximately to 15-30 seconds (e.g., 0.03 to 0.06 Hz).

CHRONOTROPIC INCOMPETENCE AND CLINICAL STRESS TEST. In an embodiment, chronotropic incompetence or "CI" or (also referred to as chronotropic insufficiency) can be observed by measuring the rate of increase of heart rate in response to physical activity measured with a motion sensor. In one particular embodiment, the motion sensor signal is used to detect periods of exercise or activity, and to trigger measurement of chronotropic incompetence, under control of instructions in the control program 124. Further, the control program 124 may be configured or programmed to implement a clinical stress test and to automatically store data during the correct time periods, with respect to periods of motion, that are appropriate for such a test.

A clinical stress test involves detecting (using a motion sensor) a rest period following exercise period, and then looking for arrhythmias only during that rest period. In contrast, CI involves detecting exercise (with a motion sensor) and then measuring rate of increase of heart rate during the exercise period itself. For CI, the system is programmed to measure heart rate during exercise, and not performing the more in-depth analysis required for detecting arrhythmias. Thus, existing heart rate algorithms can be used for measuring heart rate during exercise for CI, and the system does not necessarily need a period of ultralow motion to capture it. Specifically, in some embodiments, testing for CI may involve simultaneous measurement of exercise and heart rate. For example, the motion sensor 122 may be configured to provide an estimate of exercise intensity, and then the system may utilize existing heart rate algorithms to measure heart rate as a function of the exercise intensity.

In contrast, the clinical stress test involves a more involved process of detecting arrhythmias, which is difficult to perform during periods of high motion or exercise. For example, detecting arrhythmias involves measuring precise PPG waveform features like time between particular peaks or amplitude of the waveform etc., which is difficult to accomplish during periods of high motion or exercise. Thus, for the clinical stress test, the system is programmed or configured to measure parameters soon after exercise, since that is a time of stress without motion.

The time windows over which PPG data is observed to detect the foregoing arrhythmias may vary. For example, for detecting AF, one minute of data may be sufficient and for tachycardia or other types, a ten-second dataset may be sufficient.

4. Benefits of Certain Embodiments

Current techniques for assessment of cardiac arrhythmia require the subject to wear an electrocardiogram device such as a Holter monitor, an event recorded or even an implanted loop recorder. While such devices have high diagnostic accuracy, they are inconvenient for long term use (e.g., over months or years). In sharp contrast, embodiments described herein can be implemented using activity monitoring apparatus that is capable of conveniently wearing on the wrist, ear, head or other locations and does not require attachment of electrodes to the chest.

Some cardiac arrhythmias such as paroxysmal atrial fibrillation are relatively benign in themselves, but require long term monitoring as they raise the overall risk of stroke and other complications if not well controlled. The embodiments described herein are well suited to long term wearing and use to analyze the existence of arrhythmia over a long period, with the potential to give a patient and their doctor a sense of how well controlled their arrhythmia is.

Further, because AF is often intermittent (e.g., occurring for minutes or hours and then ending as normal sinus rhythm resumes), doctors are interested in the amount and duration of these intermittent bursts (called the AF burden) as it can help guide the treatment path (e.g., drugs or cardioversion procedures). The embodiments described herein are well suited to long-term wearing to detect the AF burden of a patient over a period of many hours or days, and are specifically capable of detecting AF episodes that other apparatus would have missed. In particular, embodiments are capable of detecting an AF episode whenever it occurs, including AF episodes that would have been missed because the patient was not wearing a Holter monitor or undergoing an EKG at the time that the AF episode occurs.

5. Hardware Overview 5.1 Activity Monitoring Device

In this embodiment, activity monitoring device comprises a wrist band in which light sources and detectors are mounted on or within an underside of the activity monitoring device. The activity monitoring device may include a fastening means to attach activity monitoring device to a portion of a user's body and the specific form of the fastening means is not critical. The fastening means may be a strap that is passed through a receiving portion of the strap and fastened with hook and/or loop fasteners. Other fastening means may include clips, latches, hook-and-loop fasteners such as VELCRO, clasps, ties, and/or adhesives. The fastening means may be located on any side of the activity monitoring device such that the fastening device does not interfere with movement or activity.

In an embodiment, the activity monitoring apparatus may comprise a processor, memory, user interface, wireless transceiver, one or more environmental sensors, and one or more biometric sensors other than the detectors. For example, embodiments may be implemented using a wearable monitor of the type shown in U.S. Pat. No. 8,948,832 of Fitbit, Inc., San Francisco, Calif., the entire contents of which are hereby incorporated by reference for all purposes as if fully set forth herein. In other words, the wearable monitor of the type shown in U.S. Pat. No. 8,948,832 could be modified based upon the additional disclosure herein to result in a working activity monitoring apparatus capable of performing the functions that are described herein. Therefore, the present disclosure presumes that the reader knows and understands U.S. Pat. No. 8,948,832, and this disclosure is directed to persons having a level of skill sufficient to modify or adapt the wearable monitor of the type shown in U.S. Pat. No. 8,948,832 based upon the additional disclosure herein to result in a working activity monitoring apparatus capable of performing the functions that are described herein.

The activity monitoring device may further comprise a display, which may be communicatively coupled to other elements through a CPU, other processor or microcontroller coupled to a memory. Display may be programmed or configured to display data such as time, heart rate, and arrhythmia events of a user. In other embodiments, the display may be omitted and data detected by the activity monitoring device may be transmitted using a wireless network transceiver via near-field communication (NFC), BLUETOOTH, WiFi, or other wireless networking protocols to a host computer for analysis, display and/or reporting.

5.2 Host Computer or Server Computer

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 9:
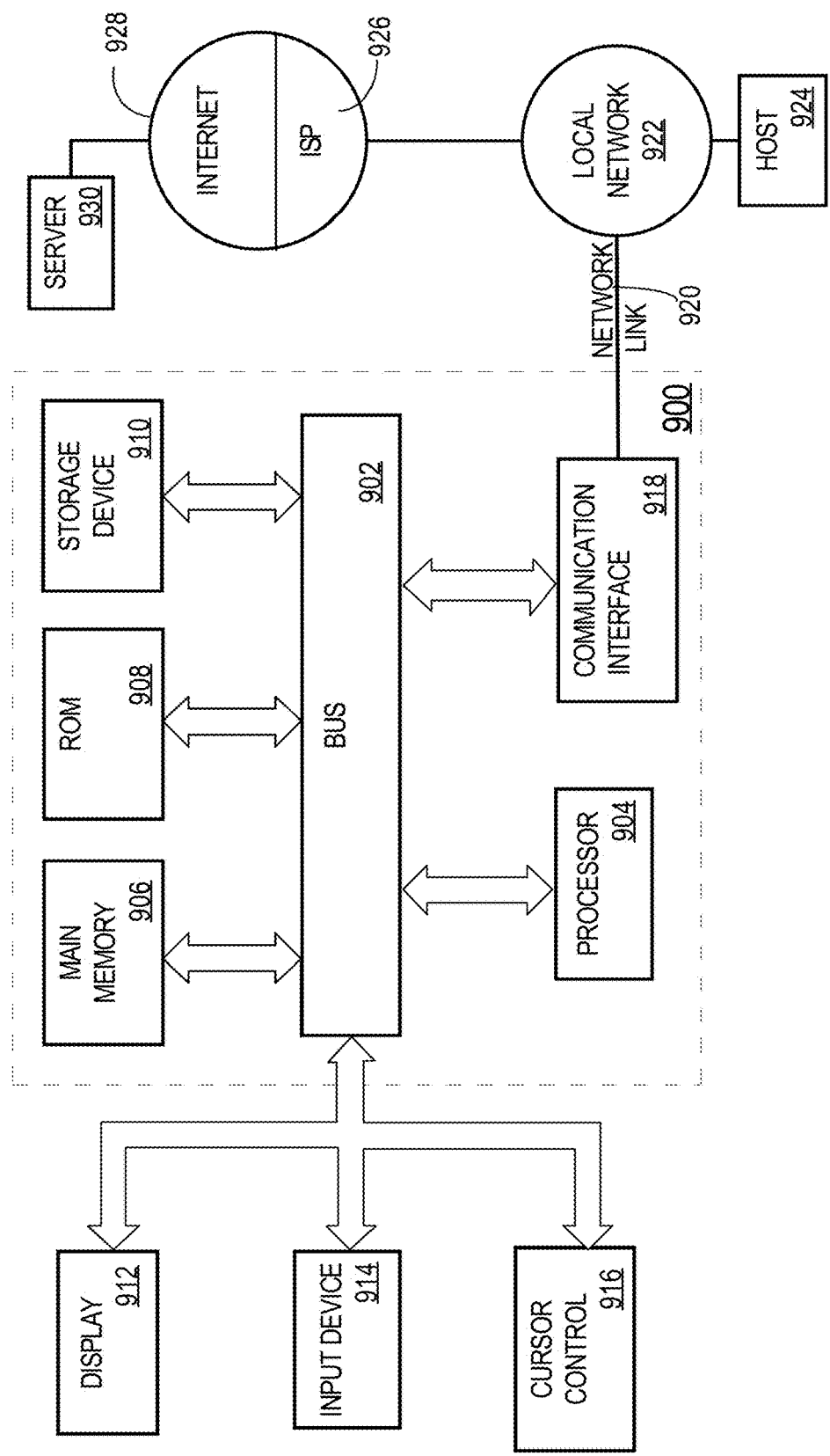
FIG. 9 is a block diagram that illustrates a computer system upon which an embodiment of the invention may be implemented.

For example, FIG. 9 is a block diagram that illustrates a computer system 900 upon which an embodiment of the invention may be implemented. Computer system 900 includes a bus 902 or other communication mechanism for communicating information, and a hardware processor 904 coupled with bus 902 for processing information. Hardware processor 904 may be, for example, a general purpose microprocessor.

Computer system 900 also includes a main memory 906, such as a random access memory (RAM) or other dynamic storage device, coupled to bus 902 for storing information and instructions to be executed by processor 904. Main memory 906 also may be used for storing temporary variables or other intermediate information during execution of instructions to be executed by processor 904. Such instructions, when stored in non-transitory storage media accessible to processor 904, render computer system 900 into a special-purpose machine that is customized to perform the operations specified in the instructions.

Computer system 900 further includes a read only memory (ROM) 908 or other static storage device coupled to bus 902 for storing static information and instructions for processor 904. A storage device 910, such as a magnetic disk, optical disk, or solid-state drive is provided and coupled to bus 902 for storing information and instructions.

Computer system 900 may be coupled via bus 902 to a display 912, such as a cathode ray tube (CRT), for displaying information to a computer user. An input device 914, including alphanumeric and other keys, is coupled to bus 902 for communicating information and command selections to processor 904. Another type of user input device is cursor control 916, such as a mouse, a trackball, or cursor direction keys for communicating direction information and command selections to processor 904 and for controlling cursor movement on display 912. This input device typically has two degrees of freedom in two axes, a first axis (e.g., x) and a second axis (e.g., y), that allows the device to specify positions in a plane.

Computer system 900 may implement the techniques described herein using customized hard-wired logic, one or more ASICs or FPGAs, firmware and/or program logic which in combination with the computer system causes or programs computer system 900 to be a special-purpose machine. According to one embodiment, the techniques herein are performed by computer system 900 in response to processor 904 executing one or more sequences of one or more instructions contained in main memory 906. Such instructions may be read into main memory 906 from another storage medium, such as storage device 910. Execution of the sequences of instructions contained in main memory 906 causes processor 904 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 910. Volatile media includes dynamic memory, such as main memory 906. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 902. Transmission media can also take the form of acoustic or light waves, such as those generated during radio-wave and infra-red data communications.

Various forms of media may be involved in carrying one or more sequences of one or more instructions to processor 904 for execution. For example, the instructions may initially be carried on a magnetic disk or solid-state drive of a remote computer. The remote computer can load the instructions into its dynamic memory and send the instructions over a telephone line using a modem. A modem local to computer system 900 can receive the data on the telephone line and use an infra-red transmitter to convert the data to an infra-red signal. An infra-red detector can receive the data carried in the infra-red signal and appropriate circuitry can place the data on bus 902. Bus 902 carries the data to main memory 906, from which processor 904 retrieves and executes the instructions. The instructions received by main memory 906 may optionally be stored on storage device 910 either before or after execution by processor 904.

Computer system 900 also includes a communication interface 918 coupled to bus 902. Communication interface 918 provides a two-way data communication coupling to a network link 920 that is connected to a local network 922. For example, communication interface 918 may be an integrated services digital network (ISDN) card, cable modem, satellite modem, or a modem to provide a data communication connection to a corresponding type of telephone line. As another example, communication interface 918 may be a local area network (LAN) card to provide a data communication connection to a compatible LAN. Wireless links may also be implemented. In any such implementation, communication interface 918 sends and receives electrical, electromagnetic or optical signals that carry digital data streams representing various types of information.

Network link 920 typically provides data communication through one or more networks to other data devices. For example, network link 920 may provide a connection through local network 922 to a host computer 924 or to data equipment operated by an Internet Service Provider (ISP) 926. ISP 926 in turn provides data communication services through the world wide packet data communication network now commonly referred to as the "Internet" 928. Local network 922 and Internet 928 both use electrical, electromagnetic or optical signals that carry digital data streams. The signals through the various networks and the signals on network link 920 and through communication interface 918, which carry the digital data to and from computer system 900, are example forms of transmission media.

Computer system 900 can send messages and receive data, including program code, through the network(s), network link 920 and communication interface 918. In the Internet example, a server 930 might transmit a requested code for an application program through Internet 928, ISP 926, local network 922 and communication interface 918.

The received code may be executed by processor 904 as it is received, and/or stored in storage device 910, or other non-volatile storage for later execution.

6. Extensions and Alternatives

In the foregoing specification, embodiments of the invention have been described with reference to numerous specific details that may vary from implementation to implementation. The specification and drawings are, accordingly, to be regarded in an illustrative rather than a restrictive sense.

Various embodiments herein describe a system which monitors the PPG signal at the wrist using an optical sensor mounted in a wristwatch form factor, using a technique referred to as reflectance photoplethysmography. Alternatively, in some embodiments, equivalent information is obtained using a finger-tip worn PPG (which uses transmittance photoplethysmography). Alternatively, in other embodiments, a valid PPG signal is obtained from other parts of the body (e.g., earlobe, forehead etc.) and utilized to determine cardiac rhythm, consistent with the techniques described herein.

Cardiac arrhythmias can also be well detected by measuring the electrical potential at the surface of the skin (e.g., electrocardiograms). This is typically done on the chest (to get best signal resolution), but can also be done by simply measuring the electrical potential across the hands. In contrast, the system described herein utilizes an optical signal instead of an electrical signal to detect arrhythmias and similar issues.

The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A method comprising:
   obtaining one or more photoplethysmography (PPG) signals from one or more PPG sensors of a monitoring apparatus, the one or more PPG signals being generated based upon optically detecting pulsed variations in blood flow;
   obtaining a motion sensor signal from a motion sensor in the monitoring apparatus;
   identifying, based upon the motion sensor signal, one or more periods of motion of the monitoring apparatus;
   selectively obtaining and storing segments of the one or more PPG signals based on a temporal relationship between the segments of the one or more PPG signals and the identified one or more periods of motion;
   determining that at least one segment of the one or more PPG signals is indicative of an arrhythmia event; and
   generating, responsive to determining that the at least one segment of the one or more PPG signals is indicative of the arrhythmia event, a notification indicating that a user of the monitoring apparatus should obtain an electrocardiogram (ECG) measurement.

2. The method of claim 1, wherein the temporal relationship indicates that the selectively obtained and stored segments of the one or more PPG signals do not correspond to the identified one or more periods of motion.

3. The method of claim 1, further comprising:
   generating and storing, based upon the segments of the one or more PPG signals, PPG waveform data identifying waveform characteristics associated with the one or more PPG signals; and
   generating and storing, based on the PPG waveform data, arrhythmia event data describing one or more arrhythmia events.

4. The method of claim 3, wherein the PPG waveform data includes a peak-to-peak dataset comprising one or more interval values representing time intervals between one or more successive peaks in the one or more PPG signals.

5. The method of claim 3, wherein the arrhythmia event data describes one or more arrhythmia types and arrhythmia durations that are associated with the one or more arrhythmia types.

6. The method of claim 1, wherein the motion sensor signal comprises one or more signals selected from the group consisting of: an accelerometer sensor signal from an accelerometer, an altitude signal from an altimeter, and a gyroscopic motion signal from a gyroscope.

7. The method of claim 1, further comprising:
   comparing a motion-related metric generated based upon the motion sensor signal to a specified motion threshold value;
   determining, based on the comparing, that the one or more periods of motion indicate low motion; and
   determining and storing one or more arrhythmia types and arrhythmia durations that are associated with the one or more arrhythmia types only during the one or more periods of motion that indicate low motion.

8. The method of claim 1, further comprising:
comparing a motion-related metric generated based upon the motion sensor signal to a specified motion threshold value;
determining, based on the comparing, that the one or more periods of motion indicate sleep; and
determining and storing one or more arrhythmia types and arrhythmia durations that are associated with the one or more arrhythmia types only during the one or more periods of motion that indicate sleep.

9. The method of claim 1, further comprising:
comparing a motion-related metric generated based upon the motion sensor signal to a specified motion threshold value;
determining, based on the comparing, that the one or more periods of motion indicate high motion; and
determining and storing, responsive to determining that the one or more periods of motion indicate high motion, one or more arrhythmia types and arrhythmia durations that are associated with the one or more arrhythmia types only during additional time periods that do not correspond to the one or more periods of motion that indicate high motion.

10. The method of claim 1, further comprising:
comparing a motion-related metric generated based upon the motion sensor signal to a specified motion threshold value;
determining, based upon the comparing, that the one or more periods of motion indicate exercise; and
determining and storing, responsive to determining that the one or more periods of motion indicate exercise, one or more arrhythmia types and arrhythmia durations that are associated with the one or more arrhythmia types only during additional time periods that do not correspond to the one or more periods of motion that indicate exercise.

11. The method of claim 10, further comprising:
obtaining, before the determining that the one or more periods of motion indicate exercise, the one or more PPG signals at a first temporal resolution;
determining, based upon the motion sensor signal, that the one or more periods of motion indicating exercise have ended and are followed by one or more periods of low motion; and
modifying, responsive to the determining that the one or more periods of motion indicating exercise have ended and are followed by one or more periods of low motion, a temporal resolution configuration parameter of the monitoring apparatus to cause the one or more PPG signals associated with the one or more periods of low motion to be obtained at a second temporal resolution that is higher than the first temporal resolution.

12. The method of claim 11, further comprising classifying, based on the obtained one or more PPG signals associated with the one or more periods of low motion, a portion of the one or more PPG signals as representing success or failure in a clinical stress test.

13. The method of claim 10, further comprising:
determining, based upon the motion sensor signal, that the one or more periods of motion indicating exercise have ended and are followed by one or more periods of low motion; and
determining and storing, responsive to determining that the one or more periods of motion indicating exercise have ended and are followed by the one or more periods of low motion, one or more arrhythmia types and arrhythmia durations that are associated with the one or more arrhythmia types during the one or more periods of low motion that follow the one or more periods of motion indicating exercise.

14. The method of claim 1, further comprising:
comparing a motion-related metric generated based upon the motion sensor signal to a specified motion threshold value;
determining, based upon the comparing, that the one or more periods of motion indicate exercise; and
identifying, responsive to determining that the one or more periods of motion indicate exercise, an instance of chronotropic incompetence based on one or more heart rate values measured during the one or more periods of motion that indicate exercise.

15. The method of claim 1, further comprising detecting one or more low amplitude PPG signals in the one or more PPG signals and, in response thereto, classifying a portion of the one or more PPG signals corresponding to the one or more low amplitude PPG signals as representing an arrhythmia.

16. The method of claim 1, further comprising:
detecting, based upon the motion sensor signal, a period of low motion of the apparatus consistent with sleep of a user over a specified time sufficient to permit detection of sleep apnea;
detecting, based on the one or more PPG signals, an indication of bradycardia; and
marking, responsive to detecting the indication of bradycardia, a portion of the one or more PPG signals corresponding to the period of low motion as representing bradycardia.

17. The method of claim 15, further comprising marking the portion of the one more PPG signals representing sleep apnea.

18. The method of claim 1, further comprising:
detecting, based upon the motion sensor signal, a period of low motion of the apparatus consistent with sleep of a user over a specified time sufficient to permit detection of sleep apnea;
detecting, based on the one or more PPG signals, an indication of tachycardia; and
marking, responsive to detecting the indication of tachycardia, a portion of the one or more PPG signals corresponding to the period of low motion as representing tachycardia.

19. The method of claim 18, further comprising marking the portion of the one or more PPG signals as representing sleep apnea.

20. The method of claim 1, further comprising:
detecting, based upon the motion sensor signal, a period of low motion of the apparatus consistent with sleep of a user;
detecting, based on the one or more PPG signals, a drop in heart rate during the period of low motion consistent with sleep; and
generating and storing, based on a) a portion of the one or more PPG signals not associated with the period of low motion consistent with sleep and b) the drop in heart rate during the period of low motion consistent with sleep, an estimate of heart rate variability.

21. The method of claim 1, further comprising classifying, based on the one or more PPG signals, a portion of the one or more PPG signals as representing atrial fibrillation.

22. The method of claim 21, further comprising generating and storing, in association with the portion of the one or more PPG signals representing atrial fibrillation, values specifying an amount and duration of atrial fibrillation.

23. The method of claim 1, further comprising:
obtaining the one or more PPG signals at a first temporal resolution; and
performing, responsive to detecting, based on the one or more PPG signals, one or more items selected from the group consisting of: cardiac chronotropic incompetence, cardiac arrhythmia, tachycardia, bradycardia, and atrial fibrillation, performing at least one action selected from the group consisting of:
modifying a temporal resolution configuration parameter of the monitoring apparatus to cause the one or more PPG signals to be obtained at a second temporal resolution that is higher than the first temporal resolution; and
outputting an alert signal.

24. A system comprising:
one or more processors coupled to electronic digital memory, the electronic digital memory storing one or more sequences of programmed instructions which, when executed by the one or more processors, cause the one or more processors to:
obtain one or more photoplethysmography (PPG) signals from one or more PPG sensors of a monitoring apparatus, the one or more PPG signals being generated based upon optical detection of pulsed variations in blood flow by the one or more PPG sensors;
obtain a motion sensor signal from a motion sensor in the monitoring apparatus;
identify, based upon the motion sensor signal, one or more periods of motion of the monitoring apparatus;
selectively obtain and store segments of the one or more PPG signals based on a temporal relationship between the segments of the one or more PPG signals and the identified one or more periods of motion;
determine that at least one segment of the one or more PPG signals is indicative of an arrhythmia event; and
generate, responsive to determining that the at least one segment of the one or more PPG signals is indicative of the arrhythmia event, a notification indicating that a user of the monitoring apparatus should obtain an electrocardiogram (ECG) measurement.

25. The system of claim 24, wherein the one or more sequences of programmed instructions, when executed by the one or more processors, further cause the one or more processors to selectively obtain an store the segments of the one or more PPG signals based on the temporal relationship indicating that the segments of the one or more PPG signals do not correspond to the identified one or more periods of motion.

26. The system of claim 24, wherein the one or more sequences of programmed instructions, when executed by the one or more processors, further cause the one or more processors to:
generate and store PPG waveform data, based upon the segments of the one or more PPG signals, identifying waveform characteristics associated with the one or more PPG signals; and
generate and store arrhythmia event data, based upon the PPG waveform data and the one or more periods of motion, describing one or more arrhythmia events.

27. The system of claim 26, wherein the PPG waveform data includes a peak-to-peak dataset comprising one or more interval values representing time intervals between one or more successive peaks in the one or more PPG signals.

28. One or more non-transitory computer-readable media storing one or more sequences of instructions which, when executed by one or more processors, cause the one or more processors to:
obtain one or more photoplethysmography (PPG) signals from one or more PPG sensors of a monitoring apparatus, the one or more PPG signals being generated based upon optically detecting pulsed variations in blood flow;
obtain a motion sensor signal from a motion sensor in the monitoring apparatus;
identify, based upon the motion sensor signal, one or more periods of motion of the monitoring apparatus;
selectively obtain and store segments of the one or more PPG signals based on a temporal relationship between the segments of the one or more PPG signals and the identified one or more periods of motion;
determine that at least one segment of the one or more PPG signals is indicative of an arrhythmia event; and
generate, responsive to determining that the at least one segment of the one or more PPG signals is indicative of the arrhythmia event, a notification indicating that a user of the monitoring apparatus should obtain an electrocardiogram (ECG) measurement.

29. The system of claim 24, wherein the monitoring apparatus is a wrist-wearable monitoring apparatus that further includes an electrocardiogram sensor having:
a first electrode that faces towards, and contacts with, a wearer's wrist when the monitoring apparatus is worn on that wrist, and
a second electrode that is separate from the first electrode and located on a surface of the monitoring apparatus on a different side of the monitoring apparatus from the first electrode, wherein the notification indicating that a user of the monitoring apparatus should obtain an electrocardiogram (ECG) measurement prompts the user to obtain the ECG measurement using the electrocardiogram sensor of the monitoring apparatus.

30. The method of claim 1, wherein:
the notification prompts the user of the monitoring apparatus to obtain the ECG measurement using an electrocardiogram sensor of the monitoring apparatus, the electrocardiogram sensor having:
a first electrode that faces towards, and contacts with, a wearer's wrist when the monitoring apparatus is worn on that wrist, and
a second electrode that is separate from the first electrode and located on a surface of the monitoring apparatus on a different side of the monitoring apparatus from the first electrode, wherein the notification indicating that a user of the monitoring apparatus should obtain an electrocardiogram (ECG) measurement prompts the user to obtain the ECG measurement using the electrocardiogram sensor of the monitoring apparatus, and
the method further comprises acquiring the ECG measurement using the electrocardiogram sensor.

* * * * *